(12) United States Patent
Kesselgruber et al.

(10) Patent No.: US 7,863,447 B2
(45) Date of Patent: Jan. 4, 2011

(54) DIPHOSPHINES AND METAL COMPLEXES

(75) Inventors: Martin Kesselgruber, Basel (CH); Marc Thommen, Nuglar (CH); Matthias Lotz, Basel (CH)

(73) Assignee: Umicore AG & Co., KG, Hanau-Wolfgang (DE)

( * ) Notice: Subject to any disclaimer, the term of this patent is extended or adjusted under 35 U.S.C. 154(b) by 691 days.

(21) Appl. No.: 11/887,448

(22) PCT Filed: Apr. 19, 2006

(86) PCT No.: PCT/EP2006/061650
§ 371 (c)(1), (2), (4) Date: Sep. 28, 2007

(87) PCT Pub. No.: WO2006/111535
PCT Pub. Date: Oct. 26, 2006

(65) Prior Publication Data
US 2009/0270622 A1 Oct. 29, 2009

(30) Foreign Application Priority Data
Apr. 20, 2005 (CH) .................................. 0708/05

(51) Int. Cl.
C07F 15/02 (2006.01)
C07F 9/02 (2006.01)
(52) U.S. Cl. ............................. 546/2; 546/21
(58) Field of Classification Search ............ 546/2, 546/21
See application file for complete search history.

(56) References Cited

U.S. PATENT DOCUMENTS

2005/0240007 A1  10/2005  Knochel et al.

FOREIGN PATENT DOCUMENTS

| WO | 03/093285 | 11/2003 |
| WO | 2005/095426 | 10/2005 |
| WO | 2005/108409 | 11/2005 |

OTHER PUBLICATIONS

International Search Report issued Nov. 2, 2006 in the International (PCT) Application of which the present application is the U.S. National Stage.
PCT Written Opinion for PCT/EP2006/061650, Sep. 28, 2007.
Matthias Lotz et al., "New Ferrocenyl Ligands with Broad Applications in Asymmetric Catalysis", Angew. Chem. Int. Ed., vol. 41, No. 24, pp. 4708-4711, XP002396743, 2002.
Armin Börner, "Chiral hydroxy phosphines as ligands for asymmetric hydrogenation and versatile building blocks for hybrid ligands", Chimica Oggi, Teknoscienze, Milano, Italy, vol. 82, pp. 48-52, XP009057245, ISSN: 0392-839X, Jun. 2000.

Primary Examiner—Charanjit S Aulakh
(74) Attorney, Agent, or Firm—Wenderoth, Lind & Ponack, L.L.P.

(57) ABSTRACT

A compound of the formula I or I',

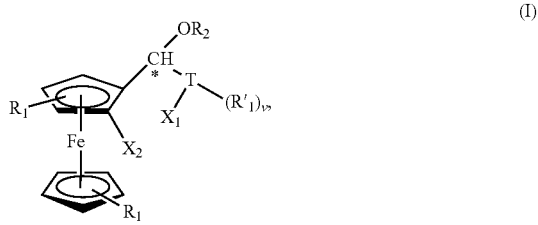

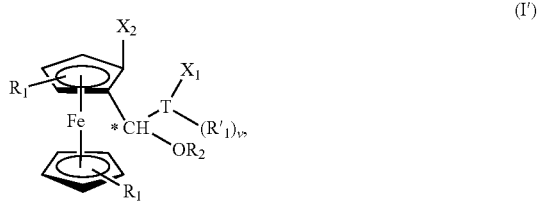

where the radicals $R_1$ are each, independently of one another, a hydrogen atom or $C_1$-$C_4$-alkyl and $R'_1$ is $C_1$-$C_4$-alkyl; $X_1$ and $X_2$ are each, independently of one another, a sec-phosphino group; $R_2$ is (1) hydrogen, (2) $R_{01}R_{02}R_{03}Si$—, (3) $C_1$-$C_{18}$-acyl substituted with halogen, hydroxyl, $C_1$-$C_8$-alkoxy or $R_{04}R_{05}N$—, or (4) $R_{06}$—$X_{01}$—C(O)—; $R_{01}$, $R_{02}$ and $R_{03}$ are each, independently of one another, $C_1$-$C_{12}$-alkyl, unsubstituted or $C_1$-$C_4$-alkyl- or $C_1$-$C_4$-alkoxy-substituted $C_6$-$C_{10}$-aryl or $C_7$-$C_{12}$-aralkyl; $R_{04}$ and $R_{05}$ are each, independently of one another, hydrogen, $C_1$-$C_{12}$-alkyl, $C_3$-$C_8$-cycloalkyl, $C_6$-$C_{10}$-aryl or $C_7$-$C_{12}$-aralkyl, or $R_{04}$ and $R_{05}$ together are trimethylene, tetramethylene, pentamethylene or 3-oxapentylene; $R_{06}$ is $C_1$-$C_{18}$-alkyl, unsubstituted or $C_1$-$C_4$-alkyl- or $C_1$-$C_4$-alkoxy-substituted $C_3$-$C_8$-cycloalkyl, $C_6$-$C_{10}$-aryl or $C_7$-$C_{12}$-aralkyl; $X_{01}$ is —O— or —NH—; T is C-bonded $C_3$-$C_{20}$-heteroarylene; v is 0 or an integer from 1 to 4; $X_1$ in the heteroring of the heteroarylene is bound in the ortho position relative to the T—C* bond; and * indicates a mixture of racemic or enantiomerically pure diastereomers or pure racemic or enantiomerically pure diastereomers.

25 Claims, No Drawings

DIPHOSPHINES AND METAL COMPLEXES

The present invention relates to 1-sec-phosphino-2-[(2'-sec-phosphino-C-heteroaromat-1'-yl)hydroxymethyl]ferrocenes as ligands for metal complexes, metal complexes of transition metals and these ligands and the use of the metal complexes for the enantioselective hydrogenation of prochiral, organic, unsaturated compounds having at least one carbon-carbon or heteroatom-carbon double bond.

Chiral diphosphines have been found to be valuable ligands for catalytically active metal complexes which are used in homogeneous catalyses for the enantioselective hydrogenation of prochiral, organic compounds in order to prepare active compounds or intermediates for active compounds, for example pharmaceuticals, pesticides or aromas including fragrances. Over the course of time, many studies have shown that the effectiveness of the catalysts in respect of optical selectivity, activity and conversion depends on the ligands and can vary more or less greatly for the same substrate as a function of the ligand. It cannot be predicted which ligands will give optimal results for a particular substrate. Efforts therefore continue to be made to provide new ligands in order to make available a broad range of ligands from which it is possible to choose ligands which give the best possible optimized conditions for a hydrogenation for particular substrates.

Among diphosphines having a ferrocene skeleton, 1-sec-phosphino-2-(2'-sec-phosphino-1'-benzyl)ferrocenes, for example, have proven to be valuable ligands for rhodium complexes for the enantioselective hydrogenation of prochiral, ethylenically unsaturated compounds. They are referred to by the trivial name TANIAPHOS and are described in WO 00/37478. The methylene group of the benzyl radical can, for example, be substituted by alkoxy or acyloxy. Substitution of the methylene group by hydroxyl is not described, nor is a description given of a synthetic route which could lead to hydroxyl-substituted ligands. WO 03/093285 describes 1-sec-phosphino-2-[(2'-sec-phosphinophen-1'-yl)-$C_1$-$C_4$-alkoxymethyl]ferrocenes in the form of diastereomers, with the stereiosomer mixture being enriched in particular enantiomers. These compounds are obtained by replacement of a sulphoxide group as chiral auxiliary group by a monohalophosphine in the presence of a strong lithium base, with hydroxybenzyl intermediates formed after addition of 1-sec-phosphinobenzaldehyde onto the ferrocene sulphoxide being converted into the alkoxy derivatives beforehand. Although the method described in WO 03/093285 was used to prepare enriched mixtures of enantiomers, no hydroxyl-substituted derivatives were prepared. Phosphino-heterocycles are generally also mentioned as ferrocene substituent in WO 03/093285, but no specific compounds are prepared and no preparative routes are indicated.

In Chirals CHIMICA OGGI/chemistry today (2000), pages 48 to 52, A. Börner states that the presence of hydroxyl groups in diphosphine ligands can influence the catalytic properties of metal complexes in respect of conversion and optical selectivity.

In ferrocenes, planar chirality is generated as a result of metallation. It has now been found that 1-sec-phosphino-2-[(2'-sec-phosphinoheteroar-1'-yl)hydroxymethyl]ferrocenes are obtained in high yields and even possibly in the form of pure enantiomers by means of simple chromatographic separation when a ferrocene having a chiral diaminophosphino group is firstly diastereoselectively metallated in the ortho position and then reacted with an ortho-sec-phosphinoaldehyde or ortho-haloheteroarylaldehyde. At this stage, the diastereomers can, if necessary, be separated in a simple manner using known methods. The further reaction to form the desired diphosphines can then be carried out in a manner known per se. It has also been surprisingly found that use of metal complexes of the hydroxy ligands in the hydrogenation of prochiral olefins gives a high catalytic activity and very high optical yields which are comparable with the results obtained using metal complexes with methoxy ligands. In addition, it has surprisingly been found that significantly higher optical yields are achieved in the hydrogenation of prochiral heteroatom-carbon double bonds, for example carbonyl groups, when using hydroxy ligands. A further advantage of the hydroxy ligands is that the hydroxyl group can be alkylated or acylated in a simple fashion to produce ligands as proposed in general terms in WO 03/093285.

The invention firstly provides compounds of the formula I or I',

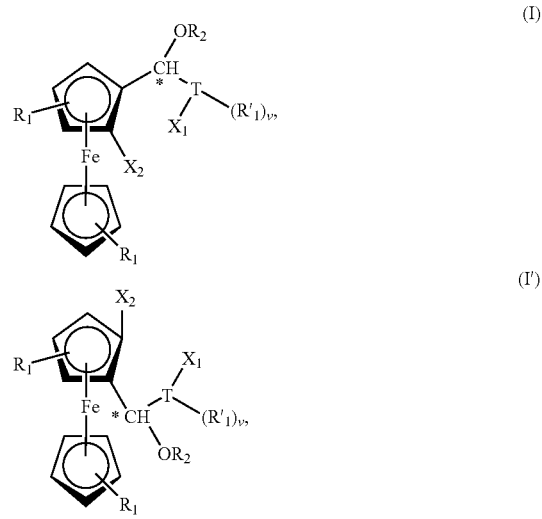

where the radicals $R_1$ are each, independently of one another, a hydrogen atom or $C_1$-$C_4$-alkyl and $R'_1$, is $C_1$-$C_4$-alkyl;

$X_1$ and $X_2$ are each, independently of one another, a sec-phosphino group;

$R_2$ is hydrogen, $R_{01}R_{02}R_{03}Si$— is with halogen-, hydroxyl-, $C_1$-$C_8$-alkoxy- or $R_{04}R_{05}N$-substituted $C_1$-$C_{18}$-acyl or is $R_{06}$—$X_{01}$—C(O)—;

$R_{01}$, $R_{02}$ and $R_{03}$ are each, independently of one another, $C_1$-$C_{12}$-alkyl, unsubstituted or $C_1$-$C_4$-alkyl- or $C_1$-$C_4$-alkoxy-substituted $C_6$-$C_{10}$-aryl or $C_7$-$C_{12}$-aralkyl;

$R_{04}$ and $R_{05}$ are each, independently of one another, hydrogen, $C_1$-$C_{12}$-alkyl, $C_3$-$C_8$-cycloalkyl, $C_6$-$C_{10}$-aryl or $C_7$-$C_{12}$-aralkyl, or $R_{04}$ and $R_{05}$ together are trimethylene, tetramethylene, pentamethylene or 3-oxapentylene;

$R_{06}$ is $C_1$-$C_{18}$-alkyl, unsubstituted or $C_1$-$C_4$-alkyl- or $C_1$-$C_4$-alkoxy-substituted $C_3$-$C_8$-cycloalkyl, $C_6$-$C_{10}$-aryl or $C_7$-$C_{12}$-aralkyl;

$X_{01}$ is —O— or —NH—;

T is C-bonded $C_3$-$C_{20}$-heteroarylene;

v is 0 or an integer from 1 to 4;

$X_1$ in the heteroring of the heteroarylene is bound in the ortho position relative to the T—C* bond; and

* indicates a mixture of racemic or enantiomerically pure diastereomers or pure racemic or enantiomerically pure diastereomers.

Very particularly preferred compounds according to the invention are compounds of the formulae Ia and Ib,

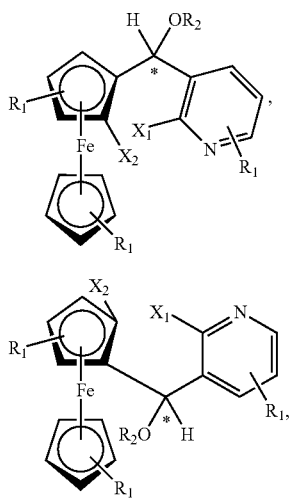

where $R_1$, $X_1$, $X_2$ and $R_2$ and * have the meanings given above.

Preference is also given to compounds according to the invention in which the group $X_1$ is bound in the ortho position relative to the heteroatom.

$R_1$ can be present from one to three times or from one to five times in the cyclopentadienyl rings. An alkyl group $R_1$ can be, for example, methyl, ethyl, n- or i-propyl, n-, i- or t-butyl, with methyl being preferred. Preference is given to $R_1$ being a hydrogen atom.

In a preferred embodiment, $R_2$ is a hydrogen atom.

An alkyl group $R_{01}$, $R_{02}$ or $R_{03}$ can be linear or branched and the alkyl preferably contains from 1 to 8 and particularly preferably from 1 to 4 carbon atoms. An aryl group $R_{01}$, $R_{02}$ or $R_{03}$ can be, for example, phenyl or naphthyl and an aralkyl group $R_{01}$, $R_{02}$ or $R_{03}$ can be benzyl or phenylethyl. Some examples of $R_{01}$, $R_{02}$ and $R_{03}$ are methyl, ethyl, n- or i-propyl, n-, i- or t-butyl, pentyl, hexyl, heptyl, octyl, nonyl, decyl, undecyl, dodecyl, phenyl, benzyl, methylphenyl, methylbenzyl, methoxyphenyl, dimethoxyphenyl and methoxybenzyl. Some preferred examples of silyl groups $R_{01}R_{02}R_{03}Si$— are trimethylsilyl, tri-n-butylsilyl, t-butyldimethylsilyl, 2,2,4,4,-tetramethylbut-4-yldimethylsilyl and triphenylsilyl.

In a preferred embodiment, $R_{04}$ and $R_{05}$ are each, independently of one another, hydrogen, $C_1$-$C_4$-alkyl, $C_5$-$C_6$-cycloalkyl, phenyl or benzyl, or $R_{04}$ and $R_{05}$ together are tetramethylene, pentamethylene or 3-oxapentyl-1,5-ene. The substituent $C_1$-$C_8$-alkoxy is preferably $C_1$-$C_4$-alkoxy such as methoxy, ethoxy, propoxy or butoxy.

An acyl group $R_2$ preferably contains from 1 to 12, and particularly preferably from 1 to 8 carbon atoms and is derived, in particular, from a carboxylic acid. Examples of such carboxylic acids are aliphatic, cycloaliphatic and aromatic carboxylic acids having from 1 to 18 and preferably from 1 to 12 carbon atoms. Some examples of substituted acyl are phenylsulphonyl, toluenesulphonyl, methylsulphonyl, phenylphosphonyl, acetyl, propanoyl, butanoyl, pentanoyl, hexanoyl, octanoyl, dodecanoyl, tetradecanoyl, octadecanoyl, cyclohexylcarbonyl, benzoyl, methylbenzoyl, phenylacetyl, pyridylcarbonyl, naphthylcarbonyl. Some examples of substituted acyl are groups of the formula $R_{07}$—C(O)—, where $R_{07}$ is hydroxymethyl, methoxymethyl, ethoxymethyl, 2-hydroxyeth-1-yl, 2-methoxyeth-1-yl, hydroxypropanoyl, fluoromethyl, chloromethyl, difluoromethyl, dichloromethyl, trifluoromethyl, trichloromethyl, aminomethyl, methylaminomethyl, dimethylaminomethyl, 1-aminoeth-1-yl, 1-methylaminoeth-1-yl, 1-dimethylaminoeth-1-yl, 2-aminoeth-1-yl, 3-aminoprop-1-yl, 4-aminobut-1-yl, pyrrolinyl-N-methyl, piperidinyl-N-methyl, morpholino-N-methyl, 4-aminocyclohex-1-yl, methoxyphenyl, hydroxyphenyl, aminophenyl, dimethylaminophenyl, hydroxybenzyl, p-aminobenzyl or p-dimethylaminobenzyl.

An alkyl group $R_{06}$ contains from 1 to 12 and particularly preferably from 1 to 8 carbon atoms. The alkyl can be linear or branched. A cycloalkyl group $R_{06}$ is preferably cyclopentyl or cyclohexyl. An aryl group $R_{06}$ can be naphthyl and in particular phenyl. An aralkyl group $R_{06}$ can be phenylethyl and in particular benzyl. Some examples of $R_{06}$ are methyl, ethyl, n- or i-propyl, n-, i- or t-butyl, pentyl, hexyl, heptyl, octyl, nonyl, decyl, undecyl, dodecyl, cyclopentyl, cyclohexyl, methylcyclohexyl, phenyl, benzyl, methylphenyl, methylbenzyl, methoxyphenyl, dimethoxyphenyl and methoxybenzyl.

A heteroarylene group T preferably contains from 4 to 14 and particularly preferably from 4 to 10 carbon atoms. It can be monocyclic or fused heteroarylene. The heteroatoms can be selected from the group consisting of —O—, —S—; —NH—, —NR$_x$— and —N═, where $R_x$ is $C_1$-$C_{12}$-alkyl, $C_5$-$C_8$-cycloalkyl, $C_5$-$C_8$-cycloalkyl-$C_1$-$C_4$-alkyl, $C_6$-$C_{10}$-aryl, $C_6$-$C_{10}$-aryl-$C_1$-$C_4$-alkyl, or a protective group such as —C(O)O$R_x$, —SO$_2R_x$, —C(O)NH$R_x$, or trialkylsilyl. Examples of heteroaryl groups from which the heteroarylene is derived are pyrrole, N-methylpyrrole, furan, thiophene, indole, N-methylindole, benzofuran, benzothiophene, pyridine, pyrimidine, and quinoline. Preference is given to pyridine, benzothiophene and indole.

The secondary phosphino groups $X_1$ and $X_2$ can each have two identical or two different hydrocarbon radicals. The secondary phosphino groups $X_1$ and $X_2$ preferably each have, independently of one another, two identical hydrocarbon radicals. Furthermore, the secondary phosphino groups $X_1$ and $X_2$ can be identical or different.

The hydrocarbon radicals can be unsubstituted or substituted and/or contain heteroatoms selected from the group consisting of O, S and N($C_1$-$C_4$-alkyl). They can contain from 1 to 22, preferably from 1 to 12 and particularly preferably from 1 to 8, carbon atoms. A preferred secondary phosphino group is one in which the phosphino group bears two identical or different radicals selected from the group consisting of linear or branched $C_1$-$C_{12}$-alkyl; unsubstituted or $C_1$-$C_6$-alkyl- or $C_1$-$C_6$-alkoxy-substituted $C_5$-$C_{12}$-cycloalkyl or $C_5$-$C_{12}$-cycloalkyl-CH$_2$—; phenyl, naphthyl, furyl and benzyl; and halogen- (for example F, Cl and Br), $C_1$-$C_6$-alkyl-, $C_1$-$C_6$-haloalkyl- (for example trifluoromethyl-), $C_1$-$C_6$-alkoxy-, $C_1$-$C_6$-haloalkoxy-(for example trifluoromethoxy-), $(C_6H_5)_3Si$—, $(C_1$-$C_{12}$-alkyl$)_3Si$—, sec-amino- or —CO$_2$—$C_1$-$C_6$-alkyl-(for example —CO$_2$CH$_3$—) substituted phenyl and benzyl.

Examples of alkyl substituents on P, which preferably contain from 1 to 6 carbon atoms, are methyl, ethyl, n-propyl, i-propyl, n-butyl, i-butyl, t-butyl, and the isomers of pentyl and hexyl. Examples of unsubstituted or alkyl-substituted cycloalkyl substituents on P are cyclopentyl, cyclohexyl, methylcyclohexyl and ethylcyclohexyl and dimethylcyclohexyl. Examples of alkyl-, alkoxy-, haloalkyl- and haloalkoxy-substituted phenyl and benzyl substituents on P are methylphenyl, dimethylphenyl, trimethylphenyl, ethylphenyl, methylbenzyl, methoxyphenyl, dimethoxyphenyl, trifluoromethylphenyl, bistrifluoromethylphenyl, tristrifluoromethylphenyl, trifluoromethoxyphenyl, bistrifluoromethoxyphenyl and 3,5-dimethyl-4-methoxyphenyl.

Preferred secondary phosphino groups are ones which bear identical radicals selected from the group consisting of $C_1$-$C_6$-alkyl, unsubstituted cyclopentyl or cyclohexyl or cyclopentyl or cyclohexyl substituted by from 1 to 3 $C_1$-$C_4$-alkyl or $C_1$-$C_4$-alkoxy groups, benzyl and in particular phenyl which may be unsubstituted or substituted by from 1 to 3 $C_1$-$C_4$-alkyl, $C_1$-$C_4$-alkoxy, F, Cl, $C_1$-$C_4$-fluoroalkyl or $C_1$-$C_4$-fluoroalkoxy groups.

The secondary phosphino group preferably corresponds to the formula —$PR_3R_4$, where $R_3$ and $R_4$ are each, independently of one another, a hydrocarbon radical which has from 1 to 18 carbon atoms and may be unsubstituted or substituted by halogen, $C_1$-$C_6$-alkyl, $C_1$-$C_6$-haloalkyl, $C_1$-$C_6$-alkoxy, $C_1$-$C_6$-haloalkoxy, ($C_1$-$C_4$-alkyl)$_2$-amino, ($C_6H_5)_3$Si, ($C_1$-$C_{12}$-alkyl)$_3$Si or —$CO_2$—$C_1$-$C_6$-alkyl and/or contains heteroatoms O.

$R_3$ and $R_4$ are preferably identical radicals selected from the group consisting of linear or branched $C_1$-$C_6$-alkyl, unsubstituted cyclopentyl and cyclohexyl or cyclopentyl and cyclohexyl substituted by from one to three $C_1$-$C_4$-alkyl or $C_1$-$C_4$-alkoxy groups, furyl, unsubstituted benzyl or benzyl substituted by from one to three $C_1$-$C_4$-alkyl or $C_1$-$C_4$-alkoxy groups and in particular unsubstituted phenyl or phenyl substituted by from one to three $C_1$-$C_4$-alkyl, $C_1$-$C_4$-alkoxy, —$NH_2$, OH, F, Cl, $C_1$-$C_4$-fluoroalkyl or $C_1$-$C_4$-fluoroalkoxy groups.

$R_3$ and $R_4$ are particularly preferably identical radicals selected from the group consisting of $C_1$-$C_6$-alkyl, cyclopentyl, cyclohexyl, furyl and unsubstituted phenyl or phenyl substituted by from one to three $C_1$-$C_4$-alkyl, $C_1$-$C_4$-alkoxy and/or $C_1$-$C_4$-fluoroalkyl groups.

The secondary phosphino groups $X_1$ and $X_2$ can be cyclic secondary phosphino, for example groups of the formulae

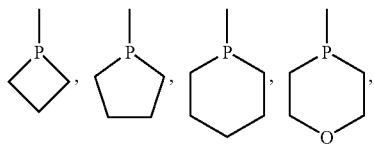

which are unsubstituted or monosubstituted or polysubstituted by —OH, $C_1$-$C_8$-alkyl, $C_4$-$C_8$-cycloalkyl, $C_1$-$C_6$-alkoxy, $C_1$-$C_4$-alkoxy-$C_1$-$C_4$-alkylphenyl, $C_1$-$C_4$-alkylphenyl or $C_1$-$C_4$-alkoxyphenyl, benzyl, $C_1$-$C_4$-alkylbenzyl or $C_1$-$C_4$-alkoxybenzyl, benzyloxy, $C_1$-$C_4$-alkylbenzyloxy or $C_1$-$C_4$-alkoxybenzyloxy, or $C_1$-$C_4$-alkylidenedioxyl.

The substituents can be present in one or both a positions relative to the P atom in order to introduce chiral carbon atoms. The substituents in one or two a positions are preferably $C_1$-$C_4$-alkyl or benzyl, for example methyl, ethyl, n- or i-propyl, benzyl or —$CH_2$—O—$C_1$-$C_4$-alkyl or —$CH_2$—O—$C_6$-$C_{10}$-aryl.

Substituents in the β, γ positions can be, for example, $C_1$-$C_4$-alkyl, $C_1$-$C_4$-alkoxy, benzyloxy, or —O—$CH_2$O—, —O—CH($C_1$-$C_4$-alkyl)-O— or —O—C($C_1$-$C_4$-alkyl)$_2$-O—. Some examples are methyl, ethyl, methoxy, ethoxy, —O—CH(methyl)-O— and —O—C(methyl)$_2$O—.

Depending on the type of substitution and number of substituents, the cyclic phosphino radicals can be C-chiral, P-chiral or C- and P-chiral.

An aliphatic 5- or 6-membered ring or benzene can be fused onto two adjacent carbon atoms in the radicals of the above formulae.

The cyclic secondary phosphino group can, for example, correspond to the formulae (only one of the possible diastereomers is indicated),

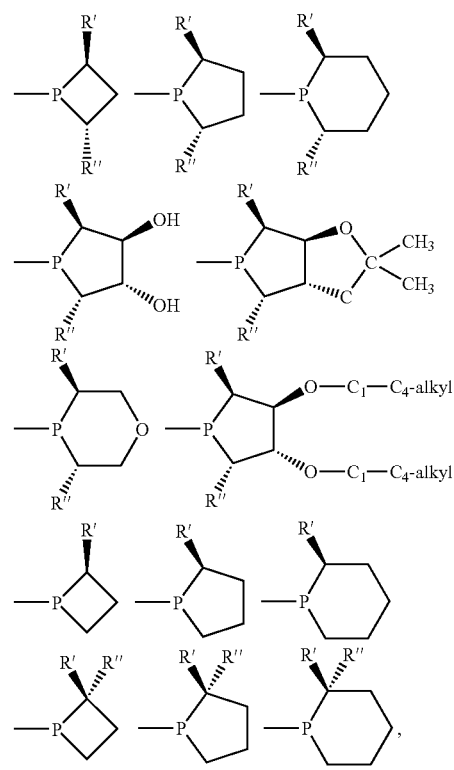

where the radicals R' and R" are each $C_1$-$C_4$-alkyl, for example methyl, ethyl, n- or i-propyl, benzyl, or —$CH_2$—O—$C_1$-$C_4$-alkyl or —$CH_2$—O—$C_6$-$C_{10}$-aryl, and R' and R" are identical or different.

In a preferred embodiment, the compounds of the invention correspond to diastereomers of the formulae Ic, Id, Ie and If,

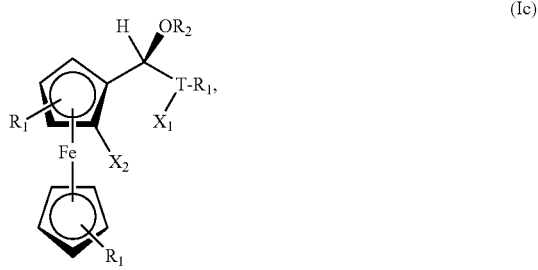

(Ic)

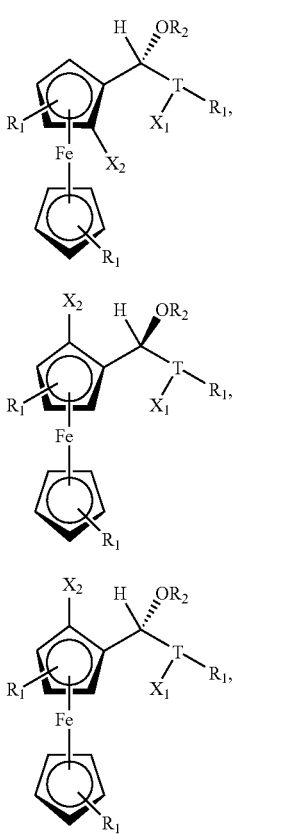

where

R₁ is hydrogen and T, R₂, X₁ and X₂ have the meanings given above, including the preferences.

In the compounds of the formulae Ic, Id, Ie and If, X₁ and X₂ are preferably identical or different acyclic secondary phosphino selected from the group consisting of —P(C₁-C₆-alkyl)₂, —P(C₅-C₈-cycloalkyl)₂, —P(C₇-C₈-bicycloalkyl)₂, —P(C₅-C₈-cycloalkyl)₂, —P(o-furyl)₂, —P(C₆H₅)₂, —P[2-(C₁-C₆-alkyl)C₆H₄]₂, —P[3-(C₁-C₆-alkyl)C₆H₄]₂, —P[4-(C₁-C₆-alkyl)C₆H₄]₂, —P[2-(C₁-C₆-alkoxy)C₆H₄]₂, —P[3-(C₁-C₆-alkoxy)C₆H₄]₂, —P[4-(C₁-C₆-alkoxy)C₆H₄]₂, —P[2-(trifluoromethyl)C₆H₄]₂, —P[3-(trifluoromethyl)C₆H₄]₂, —P[4-(trifluoromethyl)C₆H₄]₂, —P[3,5-bis(trifluoromethyl)C₆H₃]₂, —P[3,5-bis(C₁-C₆-alkyl)₂C₆H₃]₂, —P[3,5-bis(C₁-C₆-alkoxy)₂C₆H₃]₂ and —P[3,5-bis(C₁-C₄-alkyl)₂ 4-(C₁-C₆-alkoxy)C₆H₂]₂, or cyclic phosphino selected from the group consisting of

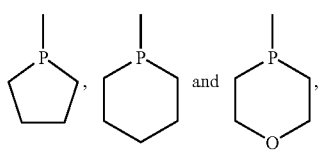

which are unsubstituted or monosubstituted or polysubstituted by C₁-C₄-alkyl, C₁-C₄-alkoxy, C₁-C₄-alkoxy-C₁-C₂-alkyl, phenyl, benzyl, benzyloxy and C₁-C₄-alkylidenedioxyl.

Some specific examples are —P(CH₃)₂, —P(i-C₃H₇)₂, —P(n-C₄H₉)₂, —P(i-C₄H₉)₂, —P(C₆H₁₁)₂, —P(norbornyl)₂, —P(o-furyl)₂, —P(C₆H₅)₂, P[2-(methyl)C₆H₄]₂, P[3-(methyl)C₆H₄]₂, —P[4-(methyl)C₆H₄]₂, —P[2-(methoxy)C₆H₄]₂, —P[3-(methoxy)C₆H₄]₂, —P[4-(methoxy)C₆H₄]₂, —P[3-(trifluoromethyl)C₆H₄]₂, —P[4-(trifluoromethyl)C₆H₄]₂, —P[3,5-bis(trifluoromethyl)C₆H₃]₂, —P[3,5-bis(methyl)₂C₆H₃]₂, —P[3,5-bis(methoxy)₂C₆H₃]₂ and —P[3,5-bis(methyl)₂₋₄-(methoxy)C₆H₂]₂ and groups of the formulae

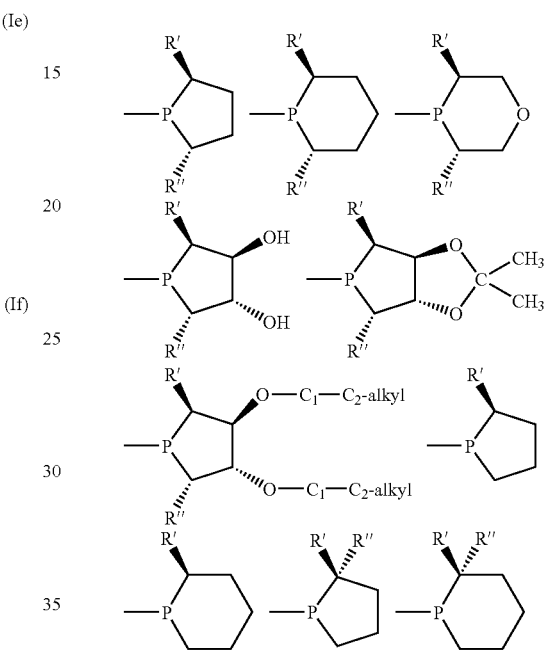

where

R' is methyl, ethyl, methoxy, ethoxy, phenoxy, benzyloxy, methoxymethyl, ethoxymethyl or benzyloxymethyl and R" has the same meanings as R'.

The ferrocenediphosphines of the invention can be prepared by means of a novel process in which a regioselective and stereoselective ortho-metallation of ferrocenylmonophosphines having P—N-bonded, chiral radicals represents the key step of the reaction sequence. The process is modular for the provision of different substituents on the two P atoms and gives high yields. In addition, pure diastereomers or pairs of easy-to-separate pairs of diastereomers can be produced directly in a simple manner and in high yields. The process is particularly useful for the preparation of the diphosphines of the invention on an industrial scale.

The preparative process comprises the following steps: in a first process step, an essentially optically pure halodi(secamino)phosphine containing chiral amino groups is provided. Such phosphines can be prepared in a simple manner by reacting PCl₃ or PBr₃ with about 2 equivalents of an optically pure, chiral, secondary amine in the presence of a halogen scavenger such as tertiary amines (triethylamine). It is advantageous to use cyclic secondary amines which have a chiral carbon atom in the α position relative to the N atom. An example is di[(S)— or (R)-α-methoxymethylpyrrolidino] chlorophosphine of the formulae

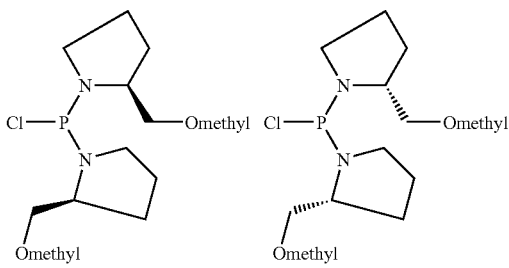

The halodi(sec-amino)phosphines are reacted with unsubstituted or $R_1$-substituted and metallated ferrocene, for example Li-ferrocene, to form compounds of the formula A

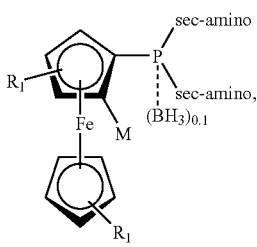
(A)

with borane being able to be introduced as protective group (for example by reaction with borane-dimethyl sulphide) prior to isolation. This intermediate is reacted in a process step a) with at least equivalent amounts of lithium alkyl, a magnesium Grignard compound or an aliphatic Li sec-amide or $X_3$Mg sec-amide to form compounds of the formula B1 or B2,

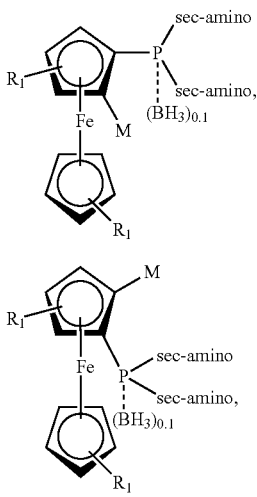
(B1)
(B2)

where

M is —Li or —$MgX_3$ and $X_3$ is Cl, Br or I. The compounds can be used in the subsequent step without intermediate isolation.

In a process step b), the compounds of the formula B1 or B2 are then reacted with at least equivalent amounts of a 1-haloheteroarene- or 1-sec-phosphinoheteroarene-2-aldehyde of the formula $$(R_1)_v T(o\text{-}X_4)\text{—}C(\!=\!O)H,$$

shown in more detail below for a preferred pyridinealdehyde of the formula C,

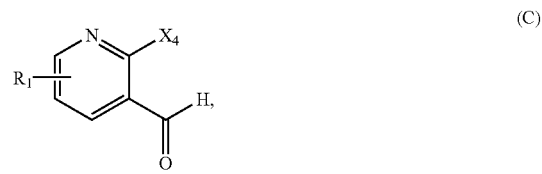
(C)

where $R_1$ is as defined above and $X_4$ is Cl, Br or I or sec-phosphino $X_1$, to form compounds of the formula D1 or D2

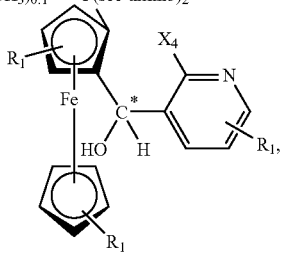
(D1)

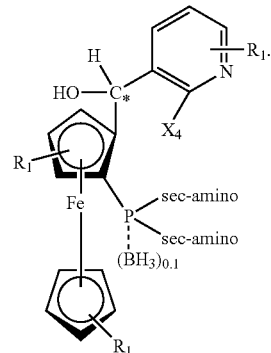
(D2)

The compounds of the formulae D1 and D2 are mixtures of diastereomers in which one can be present in excess. At this stage, pure diastereomers of the formulae D3 and D4 or D5 and D6 can easily be obtained by, for example, chromatographic methods (by means of separation on silica gels) or crystallization methods:

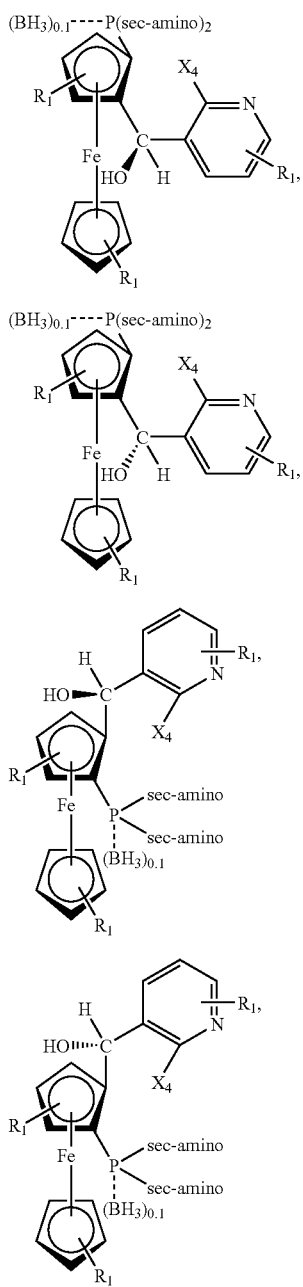

Particularly preferred haloheteroarenealdehydes have one halogen atom in the ortho position relative to the heteroatom and the aldehyde group is in turn in the α position relative to the halogen atom. Some examples are 2-chloropyridine- or 2-bromopyridine-3-aldehyde, 2-chloroquinoline- or 2-bromoquinoline-3-aldehyde, N-methyl-2-chloropyrrole- or 2-bromopyrrole-3-aldehyde, 2-chlorothiophene- or 2-bromothiophene-3-aldehyde, 2-chlorofuran- or 2-bromofuran-3-aldehyde, 2-chlorobenzothiophene- or 2-bromobenzothiophene-3-aldehyde, 2-chlorobenzofuran- or 2-bromobenzofuran-3-aldehyde, N-methyl-2-chloroindole- or 2-bromoindole-3-aldehyde.

In a next process step c), the borane group is, if present, removed from one of the compounds of the formulae D1 to D6 and the secondary amino group is then split off by means of HCl or HBr to form a —PCl$_2$ group or —PBr$_2$ group. The intermediate products can be isolated or directly reacted further to form secondary, acyclic or cyclic phosphino groups from the PCl$_2$ or PBr$_2$ groups.

As an alternative, a secondary amino group can be split off from the compounds of the formulae D1 to D6 by reaction with an acid, for example HCl, and then an alcohol, for example methanol, to form a cyclic compound, for example a compound of the formula D5 can be converted into a compound of the formula D'5:

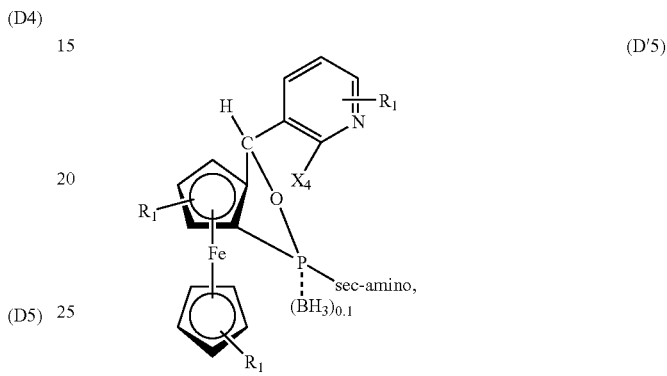

which can then be converted directly by reaction with Grignard compounds with opening of the ring into phosphino groups.

For this purpose, the Cl or Br atoms or the compound D'5 is/are reacted with at least two equivalents of an organometallic compound or one equivalent of a bisorganometallic compound (Grignard reagents) to introduce a hydrocarbon radical in a manner known per se in a process step d) to form the acyclic or cyclic secondary phosphine of the formulae E1 to E6:

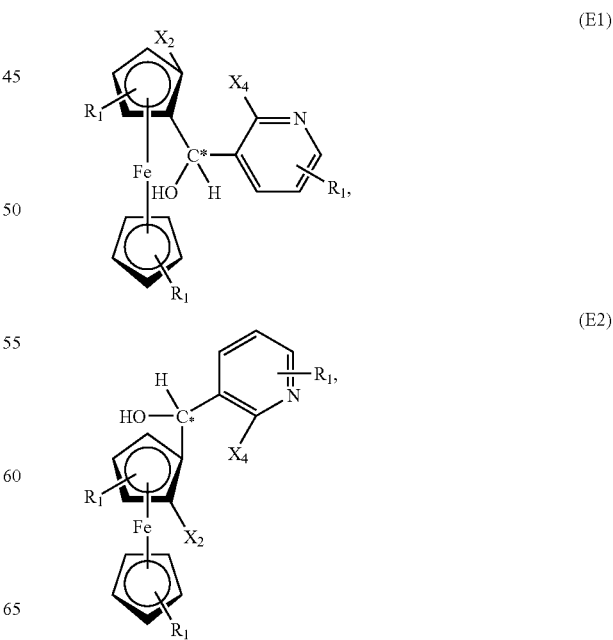

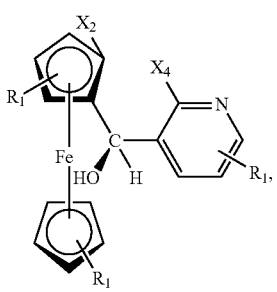
(E3)

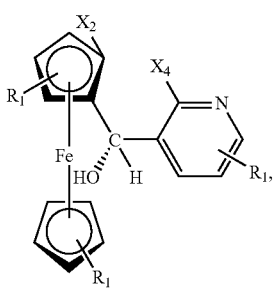
(E4)

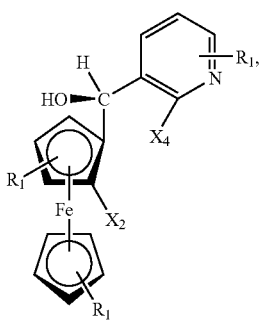
(E5)

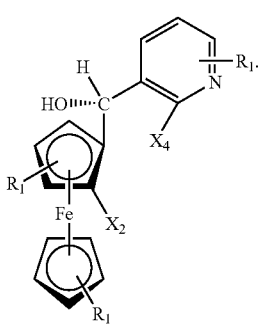
(E6)

When $X_4$ is secondary phosphino $X_1$, this step directly gives the compounds of the invention.

$PCl_2$ and $PBr_2$ groups can be hydrogenated to primary phosphino groups in a simple manner. Primary phosphino groups can then be converted in a manner known per se by means of known alkylating agents such as cyclic sulphates, sulphonates or phosphonates or open-chain disulphonates into cyclic phosphino groups.

When $X_4$ is Cl, Br or I, one of the compounds of the formulae E1 to E6 is, in a further process step e), reacted with at least 1 equivalent of lithium alkyl and then with at least 1 equivalent of secondary phosphine halide ($X_1$ halide; halide is, for example, Cl or Br) to form a compound according to the invention. As an alternative, compounds of the formulae E1 to E6 can also be reacted with preformed lithium sec-phosphide Li—$X_1$. Before these reactions, the OH group is made inert, for example by metallation with a metal hydride such as LiH, NaH or KH.

Lithium alkyl in process step a) can be, for example, Li($C_1$-$C_4$-alkyl) or phenylLi, for example methylLi, n-butylLi, s-butylLi or t-butylLi.

Aliphatic $L_1$ sec-amide or $X_3$Mg sec-amide in step a) can be derived from secondary amines containing from 2 to 18, preferably from 2 to 12 and particularly preferably from 2 to 10, carbon atoms. The aliphatic radicals bound to the N atom can be alkyl, cycloalkyl or cycloalkylalkyl or N-heterocyclic rings having from 4 to 12, and preferably from 5 to 7 carbon atoms. Examples of radicals bound to the N atom are methyl, ethyl, n-propyl, n-butyl, pentyl, hexyl, cyclopentyl, cyclohexyl and cyclohexylmethyl. Examples of N-heterocyclic rings are pyrrolidine, piperidine, morpholine, N-methylpiperazine, 2,2,6,6-tetramethylpiperidine and azanorbornane.

In a preferred embodiment, alkylLi or phenylLi are used in process step a).

The metallation of aromatics involves known reactions which are described, for example, by M. Schlosser (Editor) in Organometallics in Synthesis, Johnson Wiley & Sons (1994) or in Jonathan Clayden Organolithiums: Selectivity for Synthesis (Tetrahedron Organic Chemistry Series), Pergamon Press (2002).

For the purposes of the invention, at least equivalent amounts means the use of from 1 to 1.2 equivalents of an Li alkyl or magnesium Grignard compound or an aliphatic Li sec-amide or $X_3$Mg sec-amide per reacting =CH— group in the cyclopentadienyl ring.

The reaction is advantageously carried out at low temperatures, for example from 20 to −100° C., preferably from 10 to −50° C. The reaction time is from about 2 to 5 hours. The reaction is advantageously carried out under an inert protective gas, for example nitrogen or noble gases such as argon.

The reaction is advantageously carried out in the presence of inert solvents. Such solvents can be used either alone or as a combination of at least two solvents. Examples of solvents are aliphatic, cycloaliphatic and aromatic hydrocarbons and also open-chain or cyclic ethers. Specific examples are petroleum ether, pentane, hexane, heptane, cyclohexane, methylcyclohexane, benzene, toluene, xylene, diethyl ether, dibutyl ether, tert-butyl methyl ether, ethylene glycol dimethyl or diethyl ether, tetrahydrofuran and dioxane.

In the reaction in process step b), at least equivalent amounts means for the purposes of the invention, the use of from 1 to 1.2 equivalents of aldehyde of the formula C per reacting =CM— group in the ferrocene. However, it is also possible to use a significant excess of up to 2.5 equivalents.

The reaction is advantageously carried out at low temperatures, for example from 20 to −100° C., preferably from 0 to −80° C. The reaction is advantageously carried out under an inert protective gas, for example noble gases such as argon or else nitrogen. After addition of the compound C, the reaction mixture is advantageously allowed to warm to room temperature or is heated to elevated temperatures, for example up to 100° C. and preferably up to 50° C., and stirred for some time under these conditions to complete the reaction.

The reaction is advantageously carried out in the presence of inert solvents, for example in the abovementioned solvents.

The isolation of the compounds of the formulae D1 to D6 can be carried out by methods known per se, for example extraction, filtration and distillation. After isolation, the compounds can be purified, for example by distillation, recrystallization or chromatographic methods.

It has surprisingly been found that the reaction of the metallated and in particular lithiated ferrocenes with the prochiral compound C leads to a very high diastereoselectivity in respect of the planar chirality (ferrocene skeleton) and additionally to a significant diastereoselectivity in respect of the chirality on the prochiral carbon atom. On introduction of compound C, essentially only one pair of diastereomers in respect of planar chirality is formed among the four possible diastereomers, and it is often also observed that predominantly one diastereomer of the diastereomeric pair is preferentially formed. Pure diastereomers can, if they are necessary at all, then easily be obtained at this stage by separation by means of recrystallization or, in particular, chromatographic methods.

The reactions of process steps c) to e) are known per se and are described in the literature.

The splitting-off of the borane group can be effected, for example, by addition of reagents such as secondary amines having $C_1$-$C_4$-alkyl groups, morpholine, 1,8-diazabicyclo[5,4.0]-undec-7-ene (DBU), 1,4-diazabicyclo[2.2.2]octane, sufficiently long stirring at temperatures of from 20 to 100° C. and removal of the volatile constituents, advantageously under reduced pressure. Methods of removing borane are described, for example, by M. Ohff et al. in Synthesis (1998), page 1391. The removal of the borane group only in the last reaction step offers the advantage that reaction-sensitive groups remain protected.

The formation of —$PCl_2$ groups or —$PBr_2$ groups is likewise known and is described, for example, by A. Longeau et al. in Tetrahedron: Asymmetry, 8 (1997), pages 987-990. As reagent, use is advantageously made of organic solutions of HCl or HBr in, for example, ethers, which are added at low temperatures (for example from −20 to 30° C.) to dissolved compounds of the formula VII, IX or XI with or without a borane group.

The Grignard reagents used in process step d) can be Li—, ClMg—, BrMg— or IMg-hydro-carbons which are generally added in excess, for example up to 5 equivalents per halogen atom. The reaction is carried out in solution, with solvents as mentioned above for the metallation being able to be used. The reaction can be carried out at temperatures of from −80 to 80° C.

The reactions for introducing an acyclic or cyclic secondary phosphino group in process step e) are known per se and are illustrated in the examples.

In the compounds of the formulae E1 to E6, the OH group can, if desired, be converted into an —$OR_2$ group, for example by means of silyl halides, substituted acid derivatives such as esters and halides, carbonates or isocyanates. A large number of reagents for introducing these groups are known. As an alternative, the compounds of the formulae Ia to If in which $R_2$ is H can be converted in the same way into new ligands in which $R_2$ has the meanings indicated for the formula I with the exception of hydrogen. Known ligands in which $R_2$ is alkyl or unsubstituted acyl can be prepared analogously. To immobilize compounds according to the invention and produce catalysts which can be separated off, the compounds can be covalently bound in a known manner to a polymer via the OH group ($R_2$ is H), either directly or via a bridging group.

The invention also provides the intermediates of the formulae F and F',

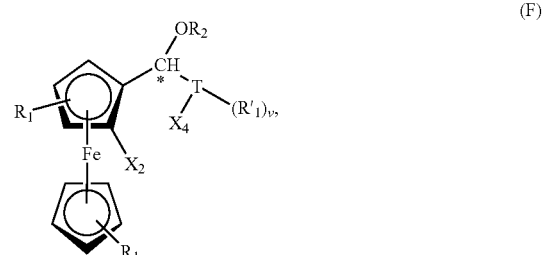

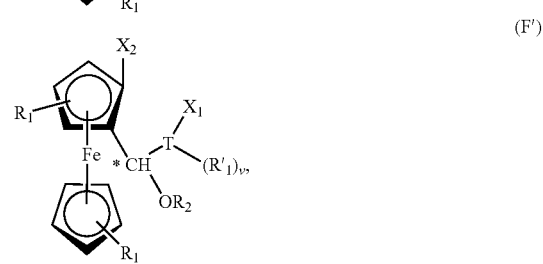

and preferably of the formulae F1 to F6

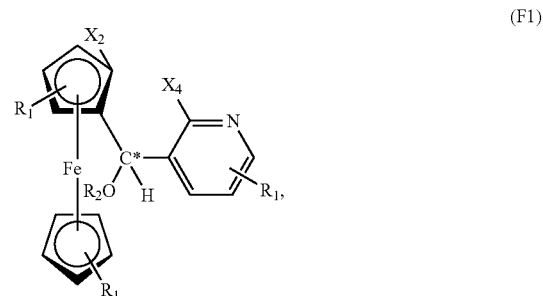

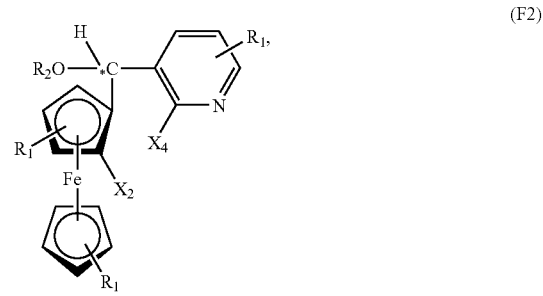

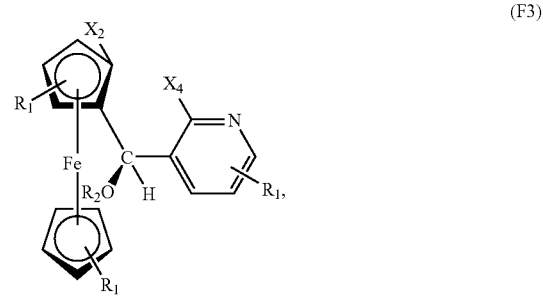

-continued

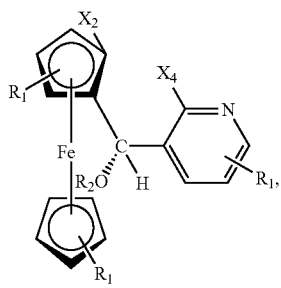
(F4)

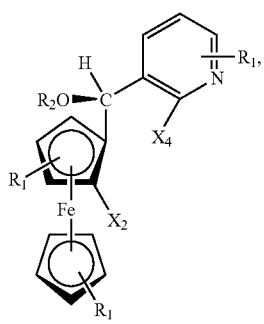
(F5)

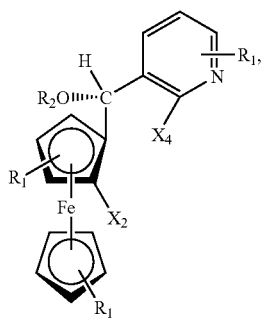
(F6)

where

T, $R_1$, $R'_1$, $X_2$ and v are as defined above, $R_2$ is H and $X_4$ is Cl, Br or I. The preferences indicated above apply to v, $R_1$, $R'_1$, $X_2$ and $X_4$.

In an alternative process, the process can start out from compounds of the formula B1 or B2 which are firstly lithiated in the ortho position by reaction with Li alkyl and then converted by reaction with dimethylformamide and subsequent hydrolysis into ferrocenealdehydes of the formula G1 or G2,

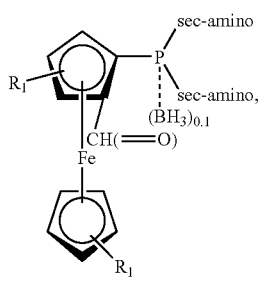
(G1)

-continued

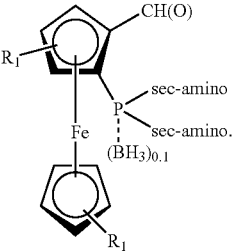
(G2)

In a next process step, the compounds of the formula G1 or G2 are then reacted with at least equivalent amounts of a 1-sec-phosphino-2-lithioheteroarene which can be obtained by lithiation of a 1-sec-phosphino-2-haloheteroarene (halogen=Cl, Br or I), illustrated below for a preferred benzothiophene of the formula,

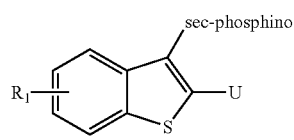

which can be reacted with G1 or G2 to form compounds of the formulae H1 and H2.

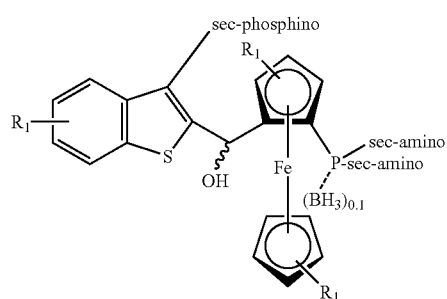
(H1)

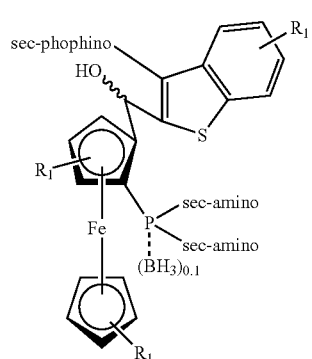
(H2)

The diastereomers can be separated at this stage or in a subsequent step. The P(sec-amino)$_2$ group can then be converted into a secondary phosphino group as described above for the compounds of the formulae D1/D2.

The inventive compounds of the formulae I and I', preferably Ia to If, are ligands to complexes of metals selected from among the group 8 transition metals, particularly preferably from the group consisting of Pd, Ru, Rh and Ir, which are excellent catalysts or catalyst precursors for asymmetric syntheses, for example the asymmetric hydrogenation of prochiral, unsaturated, organic compounds. If prochiral unsaturated organic compounds are used, a very high excess of optical isomers can be induced in the synthesis of organic compounds and a high chemical conversion can be achieved in short reaction times. The achievable enantioselectivities and catalyst activities are excellent.

The invention further provides complexes of metals selected from among the group 8 transition metals with one of the compounds of the formula I or I' and preferably Ia to If as ligands.

Possible metals are, for example, Cu, Ag, Au, Ni, Co, Rh, Pd, Ir, Ru and Pt. Preferred metals are rhodium and iridium and also ruthenium, platinum and palladium.

Particularly preferred metals are ruthenium, rhodium and iridium.

Depending on the oxidation number and coordination number of the metal atom, the metal complexes can comprise further ligands and/or anions. They can also be cationic metal complexes. Analogous metal complexes and their preparation are widely described in the literature.

The metal complexes can, for example, correspond to the general formulae II and III,

$$A_1 MeL_n \quad (II),$$

$$(A_1 MeL_n)^{(z+)}(E^-)_z \quad (III),$$

where $A_1$ is one of the compounds of the formula I or I' and preferably from Ia to If, L represents identical or different monodentate, anionic or nonionic ligands, or $L_2$ represents identical or different bidentate, anionic or nonionic ligands;

n is 2, 3 or 4 when L is a monodentate ligand or n is 1 or 2 when $L_2$ is a bidentate ligand;

z is 1, 2 or 3;

Me is a metal selected from the group consisting of Pd, Pt, Rh, Ir and Ru; with the metal being in the oxidation state 0, 1, 2, 3 or 4;

$E^-$ is the anion of an oxo acid or complex acid; and the anionic ligands balance the charge of the oxidation state 1, 2, 3 or 4 of the metals.

The above-described preferences and embodiments apply to the compounds of the formulae I and I' and Ia to If.

Monodentate nonionic ligands can, for example, be selected from the group consisting of olefins (for example ethylene, propylene), solvating solvents (nitriles, linear or cyclic ethers, unalkylated or N-alkylated amides and lactams, amines, phosphines, alcohols, carboxylic esters, sulphonic esters), nitrogen monoxide and carbon monoxide.

Suitable polydentate anionic ligands are, for example, allyls (allyl, 2-methylallyl) or deprotonated 1,3-diketo compounds such as acetylacetonate.

Monodentate anionic ligands can, for example, be selected from the group consisting of halide (F, Cl, Br, I), pseudohalide (cyanide, cyanate, isocyanate) and anions of carboxylic acids, sulphonic acids and phosphonic acids (carbonate, formate, acetate, propionate, methylsulphonate, trifluoromethylsulphonate, phenylsulphonate, tosylate).

Bidentate nonionic ligands can, for example, be selected from the group consisting of linear or cyclic diolefins (for example hexadiene, cyclooctadiene, norbornadiene), dinitriles (malonodinitrile), unalkylated or N-alkylated diamides of carboxylic acids, diamines, diphosphines, diols, dicarboxylic diesters and disulphonic diesters.

Bidentate anionic ligands can, for example, be selected from the group consisting of anions of dicarboxylic acids, disulphonic acids and diphosphonic acids (for example of oxalic acid, malonic acid, succinic acid, maleic acid, methylenedisulphonic acid and methylenediphosphonic acid).

Preferred metal complexes include ones in which E is $-Cl^-$, $-Br^-$, $-I^-$, $ClO_4^-$, $CF_3SO_3^-$, $CH_3SO_3^-$, $HSO_4^-$, $(CF_3SO_2)_2N^-$, $(CF_3SO_2)_3C^-$, tetraarylborates such as B(phenyl)$_4^-$, B[bis(3,5-trifluoromethyl)phenyl]$_4^-$, B[bis(3,5-dimethyl)phenyl]$_4^-$, B(C$_6$F$_5$)$_4^-$ and B(4-methylphenyl)$_4^-$, BF$_4^-$, PF$_6^-$, SbCl$_6^-$, AsF$_6^-$ or SbF$_6^-$.

Very particularly preferred metal complexes which are particularly suitable for hydrogenations correspond to the formulae IV and V,

$$[A_1 Me_2 YZ] \quad (IV),$$

$$[A_1 Me_2 Y]^+ E_1^- \quad (V),$$

where $A_1$ is one of the compounds of the formula I or I' and preferably Ia to If;

$Me_2$ is rhodium or iridium;

Y represents two olefins or one diene;

Z is Cl, Br or I; and $E_1^-$ is the anion of an oxo acid or complex acid.

The above-described embodiments and preferences apply to the compounds of the formulae I and I' and Ia to If.

An olefin Y can be a $C_2$-$C_{12}$-, preferably $C_2$-$C_6$- and particularly preferably $C_2$-$C_4$-olefin. Examples are propene, 1-butene and in particular ethylene. The diene can contain from 5 to 12 and preferably from 5 to 8 carbon atoms and can be an open-chain, cyclic or polycyclic diene. The two olefin groups of the diene are preferably connected by one or two CH$_2$ groups. Examples are 1,4-pentadiene, cyclopentadiene, 1,5-hexadiene, 1,4-cyclohexadiene, 1,4- or 1,5-heptadiene, 1,4- or 1,5-cycloheptadiene, 1,4- or 1,5-octadiene, 1,4- or 1,5-cyclooctadiene and norbornadiene. Y preferably represents two ethylene molecules or 1,5-hexadiene, 1,5-cyclooctadiene or norbornadiene.

In the formula XVI, Z is preferably Cl or Br. Examples of $E_1$ are BF$_4^-$, ClO$_4^-$, CF$_3$SO$_3^-$, CH$_3$SO$_3^-$, HSO$_4^-$, B(phenyl)$_4^-$, B[bis(3,5-trifluoromethyl)phenyl]$_4^-$, PF$_6^-$, SbCl$_6^-$, AsF$_6^-$ or SbF$_6^-$.

The metal complexes of the invention are prepared by methods known from the literature (cf. U.S. Pat. No. 5,371,256, U.S. Pat. No. 5,446,844, U.S. Pat. No. 5,583,241 and E. Jacobsen, A. Pfaltz, H. Yamamoto (Eds.), Comprehensive Asymmetric Catalysis I to III, Springer Verlag, Berlin, 1999, and references cited therein).

The metal complexes of the invention are homogeneous catalysts or catalyst precursors which can be activated under the reaction conditions and can be used for asymmetric addition reactions onto prochiral, unsaturated, organic compounds.

The metal complexes can, for example, be used for the asymmetric hydrogenation (addition of hydrogen) of prochiral compounds having carbon-carbon or carbon-heteroatom double bonds. Such hydrogenation using soluble homogeneous metal complexes are described, for example, in Pure and Appl. Chem., Vol. 68, No. 1, pp. 131-138 (1996). Preferred unsaturated compounds to be hydrogenated contain the groups C=C, C=N and/or C=O. According to the invention, metal complexes of ruthenium, rhodium and iridium are preferably used for the hydrogenation.

The invention further provides for the use of the metal complexes of the invention as homogeneous catalysts for preparing chiral organic compounds by asymmetric addition of hydrogen onto a carbon-carbon or carbon-heteroatom double bond in prochiral organic compounds.

A further aspect of the invention is a process for preparing chiral organic compounds by asymmetric addition of hydrogen onto a carbon-carbon or carbon-heteroatom double bond in prochiral organic compounds in the presence of a catalyst, which is characterized in that the addition reaction is carried out in the presence of catalytic amounts of at least one metal complex according to the invention.

Preferred prochiral, unsaturated compounds to be hydrogenated can contain one or more, identical or different groups C=C, C=N and/or C=O in open-chain or cyclic organic compounds, with the groups C=C, C=N and/or C=O being able to be part of a ring system or be exocydic groups. The prochiral unsaturated compounds can be alkenes, cycloalkenes, heterocycloalkenes and also open-chain or cyclic ketones, α,β-diketones, α- or β-ketocarboxylic acids and also their α,β-ketoacetals or -ketals, esters and amides, ketimines and kethydrazones.

Some examples of unsaturated organic compounds are acetophenone, 4-methoxyacetophenone, 4-trifluoromethylacetophenone, 4-nitroacetophenone, 2-chloroacetophenone, corresponding acetophenonebenzylimines and N-substituted acetophenonebenzylimines, unsubstituted or substituted benzocyclohexanone or benzocyclopentanone and corresponding imines, imines from the group consisting of unsubstituted or substituted tetrahydroquinoline, tetrahydropyridine and dihydropyrrole and unsaturated carboxylic acids, esters, amides and salts such as α- and possibly β-substituted acrylic acids or crotonic acids. Preferred carboxylic acids are those of the formula

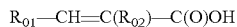

and also their salts, esters and amides, where $R_{01}$ is $C_1$-$C_6$-alkyl, $C_3$-$C_8$-cycloalkyl which may be unsubstituted or substituted by from 1 to 4 $C_1$-$C_6$-alkyl, $C_1$-$C_6$-alkoxy, $C_1$-$C_6$-alkoxy-$C_1$-$C_4$-alkoxy groups or $C_6$-$C_{10}$-aryl and preferably phenyl which may be unsubstituted or substituted by from 1 to 4 $C_1$-$C_6$-alkyl, $C_1$-$C_6$-alkoxy, $C_1$-$C_6$-alkoxy-$C_1$-$C_4$-alkoxy groups, and $R_{02}$ is linear or branched $C_1$-$C_6$-alkyl (for example isopropyl) or cyclopentyl, cyclohexyl, phenyl or protected amino (for example acetylamino) which may each be unsubstituted or substituted as defined above.

The process of the invention can be carried out at low or elevated temperatures, for example temperatures of from −20 to 150° C., preferably from −10 to 100° C. and particularly preferably from 10 to 80° C. The optical yields are generally better at low temperature than at higher temperatures.

The process of the invention can be carried out at atmospheric pressure or superatmospheric pressure. The pressure can, for example, be from $10^5$ to $2\times10^7$ Pa (pascal). Hydrogenations can be carried out at atmospheric pressure or under superatmospheric pressure.

Catalysts are preferably used in amounts of from 0.0001 to 10 mol %, particularly preferably from 0.001 to 10 mol % and very particularly preferably from 0.01 to 5 mol %, based on the compound to be hydrogenated.

The preparation of the ligands and catalysts and the hydrogenation can be carried out without solvents or in the presence of an inert solvent, with one solvent or mixtures of solvents being able to be used. Suitable solvents are, for example, aliphatic, cycloaliphatic and aromatic hydrocarbons (pentane, hexane, petroleum ether, cyclohexane, methylcyclohexane, benzene, toluene, xylene), aliphatic halogenated hydrocarbons (methylene chloride, chloroform, dichloroethane and tetrachloroethane), nitriles (acetonitrile, propionitrile, benzonitrile), ethers (diethyl ether, dibutyl ether, t-butyl-methyl ether, ethylene glycol dimethyl ether, ethylene glycol diethyl ether, diethylene glycol dimethyl ether, tetrahydrofuran, dioxane, diethylene glycol monomethyl or monoethyl ether), ketones (acetone, methyl isobutyl ketone), carboxylic esters and lactones (ethyl or methyl acetate, valerolactone), N-substituted lactams (N-methylpyrrolidone), carboxamides (dimethylamide, dimethylformamide), acyclic ureas (dimethylimidazoline) and sulphoxides and sulphones (dimethyl sulphoxide, dimethyl sulphone, tetramethylene sulphoxide, tetramethylene sulphone) and alcohols (methanol, ethanol, propanol, butanol, ethylene glycol monomethyl ether, ethylene glycol monoethyl ether, diethylene glycol monomethyl ether) and water. The solvents can be used either alone or as a mixture of at least two solvents.

The reaction can be carried out in the presence of cocatalysts, for example quaternary ammonium halides (tetrabutylammonium iodide) and/or in the presence of protic acids, for example mineral acids (cf., for example, U.S. Pat. No. 5,371,256, U.S. Pat. No. 5,446,844 and U.S. Pat. No. 5,583,241 and EP-A-0 691 949). The presence of fluorinated alcohols such as 1,1,1-trifluoroethanol can likewise promote the catalytic reaction.

The metal complexes used as catalysts can be added as separately prepared, isolated compounds or be formed in situ prior to the reaction and then mixed with the substrate to be hydrogenated. In the case of the reaction using isolated metal complexes, it can be advantageous to additionally add ligands, or in the case of the in-situ preparation, to use an excess of the ligands. The excess can be, for example, from 1 to 6 mol and preferably from 1 to 2 mol, based on the metal compound used for the preparation.

The process of the invention is generally carried out by initially charging the catalyst and then adding the substrate and if appropriate reaction auxiliaries and the compound to be added on, and subsequently starting the reaction. Gaseous compounds to be added on, for example hydrogen or ammonia, are preferably introduced by pressurizing the reaction vessel. The process can be carried out continuously or batchwise in various types of reactor.

The chiral organic compounds which can be prepared according to the invention are active substances or intermediates for preparing such substances, in particular in the field of production of aromas and fragrances, pharmaceuticals and agrochemicals.

The following examples illustrate the invention.

A) PREPARATION OF INTERMEDIATES

Example A1

Preparation of

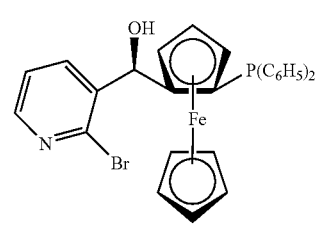

(A1)

a) Preparation of

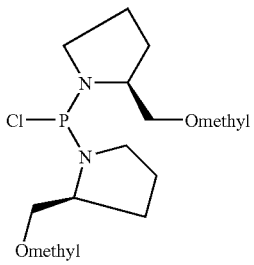

In a 500 ml round-bottom flask with argon inlet, PCl$_3$ (7.38 g, 53.75 mmol) is dissolved in dry tetrahydrofuran (THF, 150 ml) under argon and the solution is cooled to 0° C. in an ice bath. Triethylamine (11.97 g, 118.25 mmol, 2.20 equivalents) is added dropwise and (S)-methoxymethylpyrrolidine (12.69 g, 110.19 mmol, 2.05 equivalents) is subsequently slowly added dropwise. During the addition, formation of a white precipitate is observed. The ice bath is removed and the suspension obtained is stirred at room temperature (RT) overnight (14 h). The white precipitate formed is filtered off under argon by means of a double-ended frit filter and washed with dry THF (2×25 ml). A $^{31}$P-NMR(C$_6$D$_6$) spectrum of the title compound is recorded on the yellowish filtrate obtained. The solution obtained in this way is used without further purification. $^{31}$P-NMR(C$_6$D$_6$, 121 MHz): 154.3 (s).

b) Preparation of

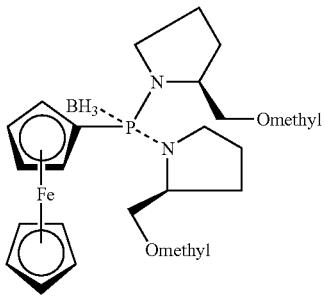

In a 1 l round-bottom flask with argon inlet, ferrocene (10.00 g, 53.75 mmol) and K t-butoxide (754 mg, 6.72 mmol, 0.125 equivalents) are dissolved in dry THF (100 ml) under argon. The solution is cooled to −78° C., and t-butylLi (1.5 M in hexane; 71.67 ml, 107.50 mmol, 2.00 equivalents) is then added dropwise over a period of 45 minutes. The solution is stirred at −78° C. for 1.5 hours and admixed with heptane (75 ml). After the precipitate formed has settled, the supernatant solution is removed at −78° C. under argon by means of a cannula. The precipitate is washed at −78° C. with heptane (60 ml) and the washings are once again removed by means of a cannula. This procedure is repeated three times. The precipitate obtained is dissolved in dry THF (50 ml) and a solution of the halophosphine prepared as described in a) (53.75 mmol, 1.00 equivalents) in THF (200 ml) is added dropwise at −78° C. over a period of 1.5 hours. The solution is stirred overnight (14 h) while warming to RT. Borane-dimethyl sulphide complex (5.10 ml, 53.75 mmol, 1.00 equivalents) is subsequently added dropwise and the mixture is stirred overnight at RT. The reaction mixture is hydrolysed by means of saturated NH$_4$Cl solution (50 ml) and extracted with tert-butyl methyl ether (TBME, 3×100 ml). The combined organic phases are dried over Na$_2$SO$_4$ and the solvent is distilled off on a rotary evaporator. The crude product (24.18 g) is purified by column chromatography (200 g of silica gel, n-heptane/TBME 5:1). The title compound is obtained as an orange solid (17.23 g, 37.60 mmol, 70%). $^1$H-NMR(C$_6$D$_6$): 4.22 (s, 5H Cp), 3.11 (s, 3H, OMe), 3.04 (s, 3H, OMe); $^{31}$P-NMR(C$_6$D$_6$, 121 MHz): 81.7-80.4 (m, br).

c) Preparation of

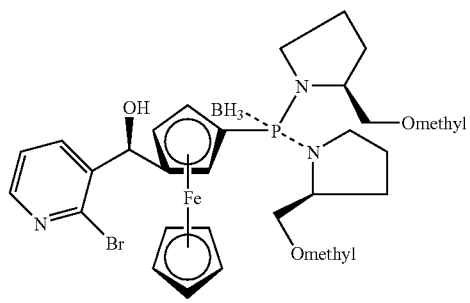

10.6 g (23.04 mmol) of the compound prepared as described in Example A1b are dissolved in 100 ml of hexane and 100 ml of MTBE and cooled to −30° C. 18.6 ml (24.10 mmol) of s-BuLi (1.3 M in cyclohexane) are added dropwise and the resulting solution is stirred at −30° C. for 2 hours, giving a yellow suspension. 4.5 g (24.19 mmol) of 2-bromopyridine-3-aldehyde are dissovled in 20 ml of THF and then added dropwise to the reaction mixture over a period of 10 minutes, and the mixture is subsequently heated to 20° C. 100 ml of water are then added, the organic phase is separated off and dried over sodium sulphate. This gives a product comprising two diastereomers (ratio=1:1). Column chromatography (heptane:MTBE, 1:1) gives 5.2 g (35%) of the title compound as a yellow solid. The fraction of the second diastereomer is not isolated. $^1$H-NMR (300 MHz, CDCl$_3$, ppm): 0.80-1.60 (b, 3H); 1.60-2.10 (m, 8H); 2.83-3.00 (m, 2H); 3.20-3.78 (m, 13H); 4.15-4.38 (m, 4H); 4.40-4.45 (m, 1H); 4.50 (s, 5H); 5.45 (d, 1H); 7.40 (dd, 1H); 8.18 (m, 1H); 8.28 (m, 1H). $^{31}$P-NMR (121.5 MHz, CDCl$_3$, ppm): 71.8.

d) Preparation of

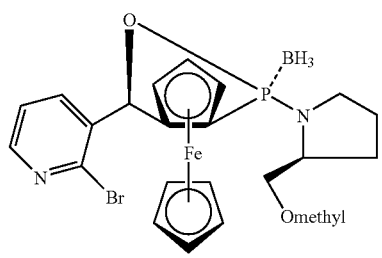

2 g (3.10 mmol) of the compound prepared as described in Example A1c are suspended in 20 ml of MTBE and cooled to −30° C. At this temperature, 7.8 ml (15.52 mmol) of HCl (2 M in diethyl ether) are added and the mixture is warmed to 20° C. 5 ml of methanol are then added and a clear orange solution is formed. 20 ml of water are added and the product is extracted with MTBE. The organic phases are dried over sodium sulphate and evaporated, giving 1.6 g (100%) of the title compound as an orange solid. $^1$H-NMR (300 MHz, $C_6D_6$, ppm): 1.20-1.73 (m, 4H); 2.75 (m, 1H); 2.94 (m, 1H); 3.17 (m, 4H); 3.18 (dd, 1H); 3.92 (s, 5H); 3.97 (m, 1H); 4.00 (m, 1H); 4.08 (m, 1H); 4.62 (m, 1H); 6.30 (s, 1H); 6.75 (dd, 1H); 7.92 (dd, 1H); 8.30 (m, 1H). $^1$P-NMR (121.5 MHz, $C_6D_6$, ppm): 112.3.

e) Preparation of the Title Compound A1

1.6 g (3.00 mmol) of the compound prepared as described in Example A1d are dissolved in 5 ml of THF and added dropwise at −78° C. to 18 ml (18.00 mmol) of phenylmagnesium bromide (1 M in THF). The mixture is slowly warmed to 20° C. and stirred at this temperature for 72 hours. 50 ml of water are then added and the mixture is extracted with MTBE. The organic phases are dried over sodium sulphate and evaporated. The crude product is dissolved in 10 ml of toluene and, after addition of 0.9 ml (6 mmol) of 1,5-diaza[5.4.0]undec-5-ene (DBU), stirred at 90° C. for 2 hours. The toluene is evaporated and the residue is purified by column chromatography (heptane:MTBE, 1:1), giving 300 mg (18%) of compound A1 as a yellow solid. $^1$H-NMR (300 MHz, $C_6D_6$, ppm): 3.00 (m, 1H); 3.75 (m, 1H); 3.94 (m, 1H); 4.06 (s, 5H); 4.14 (m, 1H); 6.06 (b, 1H); 6.44 (dd, 1H); 6.84-7.20 (m, 8H); 7.53-7.63 (m, 3H); 7.83 (dd, 1H). $^{31}$P-NMR (121.5 MHz, $C_6D_6$, ppm): −22.4.

Example A2

Preparation of

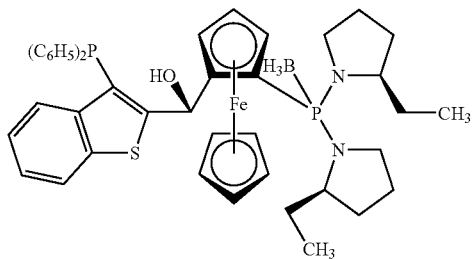

a) Preparation of

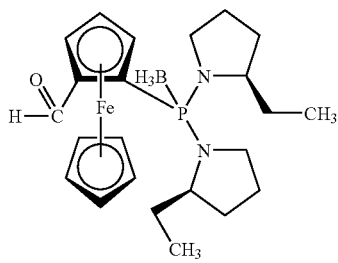

1.1 g (2.30 mmol) of the compound from Example A1 b are dissolved in 10 ml of hexane and 10 ml of methyl t-butyl ether and cooled to −30° C. 1.9 ml (2.41 mmol) of s-butylLi (1.3 M in cyclohexane) are then added dropwise and the resulting solution is stirred at −30° C. for 2 hours, giving a yellow suspension. 0.18 g (2.41 mmol) of dry dimethylformamide is then dissolved in 2 ml of tetrahydrofuran and the solution is added dropwise over a period of 10 minutes to the reaction mixture which is subsequently warmed to 20° C. 100 ml of water are then added, the organic phase is separated and dried over sodium sulphate. The two diastereomers, which are formed in a ratio of 1:1, are separated by column chromatography (heptane:methyl t-butyl ether=1:1). This gives 0.5 g (43%) of the title compound as a red, wax-like solid. $^1$H-NMR (300 MHz, $C_6D_6$, ppm): 1.20-2.00 (m, 12H); 2.53-2.66 (m, 2H); 2.88-2.95 (m, 2H); 3.04 (s, 3H); 3.10-3.23 (m, 2H); 3.25 (s, 3H); 3.37-3.57 (m, 2H); 4.25-4.32 (m, 2H); 4.37 (s, 5H); 4.48 (b, 1H); 5.08 (b, 1H); 10.68 (s, 1H). $^{31}$P-NMR (121.5 MHz, C6D6, ppm): 73.1.

b) Preparation of 3-diphenylphosphino[1,2-b]benzothiophene

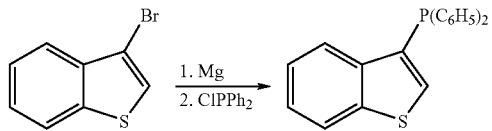

2 g (9.39 mmol) of 3-bromobenzo[1,2-b]thiophene are reacted with 292 mg (12 mmol) of magnesium turnings in 20 ml of tetrahydrofuran. 1.99 g (9 mmol) of chlorodiphenylphosphine are then added dropwise at 0° C. and the mixture is subsequently stirred for 2 hours. The mixture is admixed with 2M HCl while stirring and extracted with ethyl acetate. The organic phases are dried over sodium sulphate and evaporated, giving 2.1 g (70%) of the title compound as a beige powder. $^{31}$P-NMR (121.5 MHz, $C_6D_6$, ppm): −20.7.

c) Preparation of

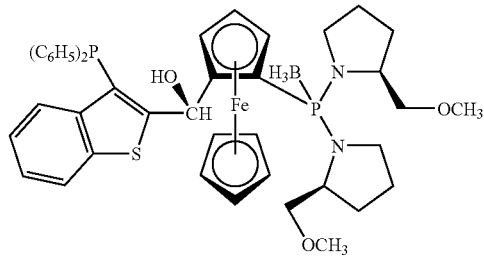

0.27 ml (1.92 mmol) of diisopropylamine is dissolved in 2 ml of tetrahydrofuran and cooled to −10° C. 0.74 ml (1.85 mmol) of 2.5 M n-butylLi is then added and the solution is stirred at 0° C. for 15 minutes. 588 mg (1.85 mmol) of the compound from Example A2b are then added at −15° C. and the solution is stirred for 45 minutes. 940 mg (1.92 mmol) of the compound from Example A2a are dissolved in 4 ml of tetrahydrofuran and slowly added dropwise to the first solution. The reaction mixture is stirred at room temperature for 12 hours. The solvent is evaporated and the crude product is purified by chromatography over silica gel (eluent heptane: methyl t-butyl ether=2:1), giving 265 mg (18%) of the title compound as a yellow solid. $^1$H-NMR (300 MHz, $C_6D_6$, ppm): 1.20-2.06 (m, 14H); 2.78-2.88 (m, 1H); 3.04 (s, 3H); 3.05-3.13 (m, 3H); 3.26 (s, 3H); 3.28-3.42 (m, 2H); 3.60 (dd, 1H); 3.84 (t, 1H); 3.90 (b, 1H); 4.24 (b, 1H); 4.35-4.54 (m, 2H); 4.67 (s, 5H); 5.02 (d, 1H); 6.77-7.05 (m, 8H); 7.32-7.72 (m, 6H). $^{31}$P-NMR (121.5 MHz, $C_6D_6$, ppm): −28.3; 72.1.

B) PREPARATION OF DIPHOSPHINES

Example B1

Preparation of (S)-1-diphenylphosphino-2-[α-(S)-hydroxy(2-diphenylphosphino-3-pyridinyl)methyl] ferrocene of the Formula B1

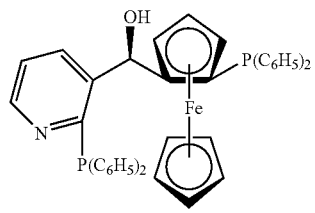

(B1)

At 0° C., 0.05 ml (0.432 mmol) of KH suspension (35% in oil) is suspended in 2 ml of THF and 150 mg (0.270 mmol) of compound A1 dissolved in 2 ml of THF are added dropwise. The mixture is stirred at 20° C. for 1 hour and then cooled to 0° C. 0.06 ml (0.316 mmol) of chlorodiphenylphosphine is slowly added dropwise and the mixture is stirred at 0° C. for 1 hour. The reaction mixture is cooled to −78° C. and 0.40 ml (0.599 mmol) of t-butyllithium (1.5 M in pentane) is added dropwise. The mixture is warmed to 20° C. over a period of 1 hour and is then admixed with water. The mixture is extracted with MTBE, the organic phases are dried over sodium sulphate and purified by column chromatography (heptane:MTBE, 1:1), giving 52 mg (29%) of compound B1 as a light-yellow solid. $^1$H-NMR (300 MHz, $C_6D_6$, ppm): 3.10 (m, 1H); 3.80 (m, 1H); 3.96 (m, 1H); 4.07 (s, 5H); 4.13 (m, 1H); 6.50 (dd, 1H); 6.85-7.08 (m, 14H); 7.53-7.73 (m, 8H); 8.24 (m, 1H). $^{31}$P-NMR (121.5 MHz, $C_6D_6$, ppm): −22.3; −13.0.

Example B2

Preparation of

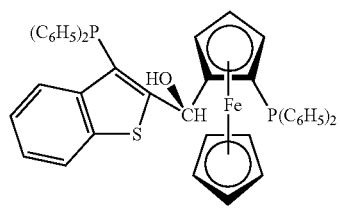

(B2)

265 mg (0.33 mmol) of the compound from Example A2c are dissolved in 3 ml of methyl t-butyl ether and admixed at −70° C. with 1.54 ml (6.16 mmol) of HCl in dioxane (4 M). After 30 minutes, the suspension is filtered and the filtrate is admixed at −70° C. with 2 ml (4 mmol) of $C_6H_5MgCl$ (2M in tetrahydrofuran). The mixture is warmed to room temperature over a period of 12 hours and admixed with 2M hydrochloric acid while stirring. The product is extracted with methyl t-butyl ether, the organic phases are dried over sodium sulphate, filtered and the solvent is then evaporated. The crude product is prepurified by means of column chromatography (silica gel, heptane:methyl t-butyl ether=2:1). The crude product is dissolved in 2 ml of toluene, admixed with 0.05 ml of DBU and heated at 80° C. for 5 hours while stirring. The solution is evaporated, the residue is taken up in methyl t-butyl ether and extracted with 2M hydrochloric acid. The organic phases are dried over sodium sulphate and evaporated. This gives 20 mg (9%) of the title compound. $^{31}$P-NMR (121.5 MHz, $C_6D6$, ppm): −26.7; −21.4. MS (ESI): 717 ($M^+$, 100%).

C) PREPARATION OF METAL COMPLEXES

General method: a catalyst solution is prepared in a Schlenk vessel filled with argon by dissolving, for example, 4.73 mg (0.01265 mmol) [Rh(norbornadiene)$_2$]BF$_4$ or another metal complex and 8.96 mg (0.0133 mmol) of diphosphine ligand in 5 ml of degassed methanol.

D) USE EXAMPLES

Example D1

Hydrogenation of methyl cis-acetamidocinnamate 0.555 g (2.53 mmol) of methyl cis-acetamidocinnamate and 5 ml of degassed methanol are introduced in succession into a Schlenk vessel filled with argon. In a second Schlenk vessel filled with argon, a catalyst solution comprising 4.73 mg (0.01265 mmol) of [Rh(norbornadiene)$_2$]BF$_4$, 8.77 mg (0.0133 mmol) of ligand B1 and 5 ml of degassed methanol is prepared. This solution and the catalyst solution are then transferred in succession by means of a steel capillary into a 50 ml glass reactor filled with argon. The ratio of substrate/catalyst (s/c) is 200. The reactor is closed and a pressure of 1.00 bar is set by means of 4 flushing cycles (pressurization to 1 bar of hydrogen). The autoclave is thermostated at 25° C. and the reaction is started by switching on the stirrer. The reactor is stirred for 1 hour. After opening the reactor, a reddish reaction solution is isolated. The conversion is quantitative (determined by means of GC and $^1$H-NMR). Removal of the solvent on a rotary evaporator gives a quantitative yield of the methyl ester of (S)—N-acetylphenylalanine having an enantiomeric purity of 97.4% ee (determined by means of GC; column: Chirasil-L-Val.).

Example D2

Hydrogenation of dimethyl itaconate

The procedure of Example D1 is repeated using 0.4 g (2.53 mmol) of dimethyl itaconate as starting material and 8.77 mg (0.0133 mmol) of compound B1 as ligand. The conversion is 100%. Removal of the solvent on a rotary evaporator gives a quantitative yield of (2R)-dimethyl succinate having an enantiomeric purity of 99.5% ee.

Example D3

Hydrogenation of ethyl 3-oxovalerate

The procedure of Example D1 is repeated using ethanol as solvent. The reaction temperature is 80° C. and the hydrogen pressure is 80 bar. 0.4 g (2.53 mmol) of ethyl 3-oxovalerate is used as starting material, 8.77 mg (0.0133 mmol) of compound BI are used as ligand and [RuI$_2$(p-cymene)]$_2$ is used as metal complex. The ratio of substrate to catalyst (s/c) is 400. The conversion is over 90%. Removal of the solvent on a rotary evaporator gives ethyl (3R)-hydroxyvalerate having an enantiomeric purity of 90.4% ee.

Example D4

Hydrogenation of ethyl 3-oxo-3-phenylpropionate

The procedure of Example D1 is repeated using ethanol as solvent. The reaction temperature is 80° C. and the hydrogen pressure is 80 bar. 0.4 g (2.53 mmol) of ethyl 3-oxo-3-phenylpropionate is used as starting material, 8.77 mg (0.0133 mmol) of compound B1 are used as ligand and [RuI$_2$(p-cymene)]$_2$ is used as metal complex. The ratio of substrate to catalyst (s/c) is 400. The conversion is over 90%. Removal of the solvent on a rotary evaporator gives ethyl (3R)-hydroxy-3-phenylpropionate having an enantiomeric purity of 40.3% ee.

The invention claimed is:

1. A compound of the formula I or I',

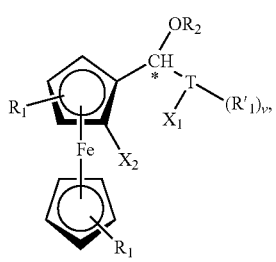

(I)

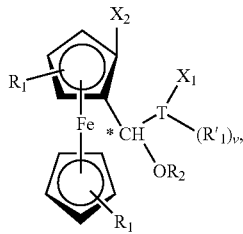

(I')

where the radicals R$_1$ are each, independently of one another, a hydrogen atom or C$_1$-C$_4$-alkyl and R'$_1$ is C$_1$-C$_4$-alkyl;

X$_1$ and X$_2$ are each, independently of one another, a sec-phosphino group;

R$_2$ is (1) hydrogen, (2) R$_{01}$R$_{02}$R$_{03}$Si—, (3) C$_1$-C$_{18}$-acyl substituted with halogen, hydroxyl, C$_1$-C$_8$-alkoxy or R$_{04}$R$_{05}$N—, or (4) R$_{06}$—X$_{01}$—C(O)—;

R$_{01}$, R$_{02}$ and R$_{03}$ are each, independently of one another, C$_1$-C$_{12}$-alkyl, unsubstituted or C$_1$-C$_4$-alkyl- or C$_1$-C$_4$-alkoxy-substituted C$_6$-C$_{10}$-aryl or C$_7$-C$_{12}$-aralkyl;

R$_{04}$ and R$_{05}$ are each, independently of one another, hydrogen, C$_1$-C$_{12}$-alkyl, C$_3$-C$_8$-cycloalkyl, C$_6$-C$_{10}$-aryl or C$_7$-C$_{12}$-aralkyl, or R$_{04}$ and R$_{05}$ together are trimethylene, tetramethylene, pentamethylene or 3-oxapentylene;

R$_{06}$ is C$_1$-C$_{18}$-alkyl unsubstituted or C$_1$-C$_4$-alkyl- or C$_1$-C$_4$-alkoxy-substituted C$_3$-C$_8$-cycloalkyl, C$_6$-C$_{10}$-aryl or C$_7$-C$_{12}$-aralkyl;

X$_{01}$ is —O— or —NH—;

T is C-bonded C$_3$-C$_{20}$-heteroarylene;

v is 0 or an integer from 1 to 4;

X$_1$ in the heteroring of the heteroarylene is bound in the ortho position relative to the T—C* bond; and

* indicates a mixture of racemic or enantiomerically pure diastereomers or pure racemic or enantiomerically pure diastereomers.

2. A compound according to claim 1, wherein the compound has the formulae Ia or Ib,

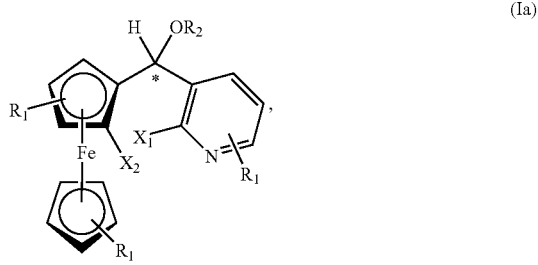

(Ia)

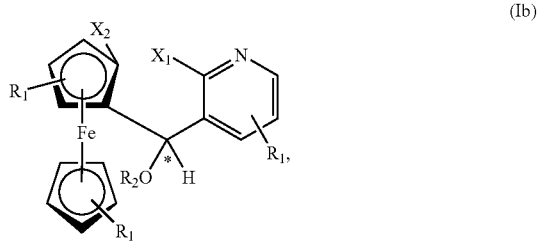

(Ib)

where R$_1$, X$_1$, X$_2$ and R$_2$ and * have the meanings given in claim 1.

3. A compound according to claim 1, wherein R$_1$ is a hydrogen atom.

4. A compound according to claim 1, characterized in wherein an alkyl group R$_{01}$, R$_{02}$ and R$_{03}$ contains from 1 to 8 carbon atoms, an aryl group R$_{01}$, R$_{02}$ or R$_{03}$ is phenyl or naphthyl and an aralkyl group R$_{01}$, R$_{02}$ or R$_{03}$ is benzyl or phenylethyl.

5. A compound according to claim 1, wherein R$_{04}$ and R$_{05}$ are each, independently of one another, hydrogen, C$_1$-C$_4$-alkyl, C$_5$-C$_6$-cycloalkyl, phenyl or benzyl, or R$_{04}$ and R$_{05}$ together are tetramethylene, pentamethylene or 3-oxapentyl-1,5-ene.

6. A compound according to claim 1, wherein acyl groups R$_2$ are derived from carboxylic acids.

7. A compound according to claim 1, characterized in wherein an alkyl group R$_{06}$ contains from 1 to 12 carbon atoms, a cycloalkyl group R$_{06}$ is cyclopentyl or cyclohexyl, an aryl group R$_{06}$ is naphthyl or phenyl and an aralkyl group R$_{06}$ is phenylethyl or benzyl.

8. A compound according to claim 1, wherein the secondary phosphino groups X$_1$ and X$_2$ each have two identical hydrocarbon radicals.

9. A compound according to claim 1, wherein the secondary phosphino groups X$_1$ and X$_2$ are identical or different.

10. A compound according to claim 1, wherein the secondary phosphino groups X$_1$ and X$_2$ contain hydrocarbon radicals which have from 1 to 22 carbon atoms and may be unsubstituted or substituted and/or contain heteroatoms selected from the group consisting of O, S and N(C$_1$-C$_4$-alkyl).

11. A compound according to claim 10, wherein the secondary phosphino group bears two identical or different hydrocarbon radicals selected from the group consisting of linear or branched $C_1$-$C_{12}$-alkyl; unsubstituted or $C_1$-$C_6$-alkyl- or $C_1$-$C_6$-alkoxy-substituted $C_5$-$C_{12}$-cycloalkyl or $C_5$-$C_{12}$-cycloalkyl-$CH_2$—; phenyl, naphthyl, furyl and benzyl; and halogen-, $C_1$-$C_6$-alkyl-, $C_1$-$C_6$-haloalkyl-, $C_1$-$C_6$-alkoxy-, $C_1$-$C_6$-haloalkoxy-, $(C_6H_5)_3Si$—, $(C_1$-$C_{12}$-alkyl$)_3$Si—, sec-amino- or —$CO_2$—$C_1$-$C_6$-alkyl-substituted phenyl and benzyl.

12. A compound according to claim 1, wherein the secondary phosphino group corresponds to the formula —$PR_3R_4$, where $R_3$ and $R_4$ are each, independently of one another, a hydrocarbon radical which has from 1 to 18 carbon atoms and may be unsubstituted or substituted by halogen, $C_1$-$C_6$-alkyl, $C_1$-$C_6$-haloalkyl, $C_1$-$C_6$-alkoxy, $C_1$-$C_6$-haloalkoxy, $(C_1$-$C_4$-alkyl$)_2$-amino, $(C_6H_5)_3Si$, $(C_1$-$C_{12}$-alkyl$)_3$Si or —$CO_2$—$C_1$-$C_6$-alkyl and/or contains heteroatoms O.

13. A compound according to claim 1, wherein the secondary phosphino groups $X_1$ and $X_2$ are cyclic secondary phosphino.

14. A compound according to claim 13, wherein the cyclic secondary phosphino corresponds to one of the formulae

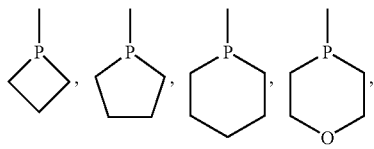

where the rings are unsubstituted or monosubstituted or polysubstituted by —OH, $C_1$-$C_8$-alkyl, $C_4$-$C_8$-cycloalkyl, $C_1$-$C_6$-alkoxy, $C_1$-$C_4$-alkoxy-$C_1$-$C_4$-alkyl, phenyl, $C_1$-$C_4$-alkylphenyl or $C_1$-$C_4$-alkoxyphenyl, benzyl, $C_1$-$C_4$-alkylbenzyl or $C_1$-$C_4$-alkoxybenzyl, benzyloxy, $C_1$-$C_4$-alkylbenzyloxy or $C_1$-$C_4$-alkoxybenzyloxy, or $C_1$-$C_4$-alkylidenedioxyl.

15. A compound according to claim 1, which corresponds to the diastereomer of the formulae Ic, Id, Ie or If,

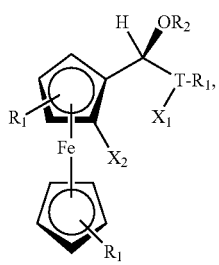

(Ic)

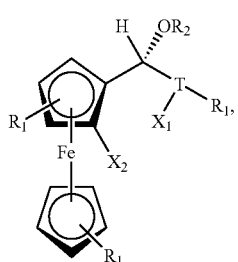

(Id)

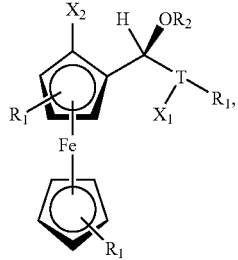

(Ie)

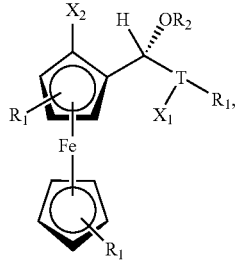

(If)

where
$R_1$ is hydrogen and T, $R_2$, $X_1$ and $X_2$ have the meanings given in claim 1.

16. A compound according to claim 15, wherein, in the formulae Ic, Id, Ie and If, $X_1$ and $X_2$ are preferably identical or different acyclic secondary phosphino selected from the group consisting of —$P(C_1$-$C_6$-alkyl$)_2$, —$P(C_5$-$C_8$-cycloalkyl$)_2$, —$P(C_7$-$C_8$-bicycloalkyl$)_2$, —$P(C_5$-$C_8$-cycloalkyl$)_2$, —$P(o$-furyl$)_2$, —$P(C_6H_5)_2$, —$P[2$-$(C_1$-$C_6$-alkyl$)C_6H_4]_2$, —$P[3$-$(C_1$-$C_6$-alkyl$)C_6H_4]_2$, —$P[4$-$(C_1$-$C_6$-alkyl$)C_6H_4]_2$, —$P[2$-$(C_1$-$C_6$-alkoxy$)C_6H_4]_2$, —$P[3$-$(C_1$-$C_6$-alkoxy$)C_6H_4]_2$, —$P[4$-$(C_1$-$C_6$-alkoxy$)C_6H_4]_2$, —$P[2$-(trifluoromethyl$)C_6H_4]_2$, —$P[3$-(trifluoromethyl$)C_6H_4]_2$, —$P[4$-(trifluoromethyl$)C_6H_4]_2$, —$P[3,5$-bis(trifluoromethyl$)C_6H_3]_2$, —$P[3,5$-bis$(C_1$-$C_6$-alkyl$)_2C_6H_3]_2$, —$P[3,5$-bis$(C_1$-$C_6$-alkoxy$)_2C_6H_3]_2$ and —$P[3,5$-bis$(C_1$-$C_6$-alkyl$)_{2\text{-}4}$-$(C_1$-$C_6$-alkoxy$)C_6H_2]_2$, or identical or different cyclic phosphino selected from the group consisting of

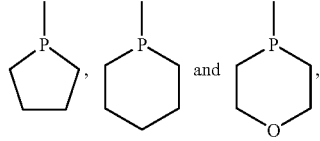

where the rings are unsubstituted or monosubstituted or polysubstituted by HO, $C_1$-$C_4$-alkyl, $C_1$-$C_4$-alkoxy, $C_1$-$C_4$-alkoxy-$C_1$-$C_2$-alkyl, phenyl, benzyl, benzyloxy and $C_1$-$C_4$-alkylidenedioxyl.

17. A compound according to claim 15, wherein secondary phosphino groups $X_1$ and $X_2$ are —$P(CH_3)_2$, —$P(i$-$C_3H_7)_2$, —$P(n$-$C_4H_9)_2$, —$P(i$-$C_4H_9)_2$, —$P(C_6H_{11})_2$, —$P(norbornyl)_2$, —$P(o$-furyl$)_2$, —$P(C_6H_5)_2$, $P[2$-(methyl$)C_6H_4]_2$, $P[3$-(methyl$)C_6H_4]_2$, —$P[4$-(methyl$)C_6H_4]_2$, —$P[2$-(methoxy$)C_6H_4]_2$, —$P[3$-(methoxy$)C_6H_4]_2$, —$P[4$-(methoxy$)C_6H_4]_2$, —$P[3$-(trifluoromethyl$)C_6H_4]_2$, —$P[4$-(trifluoromethyl$)C_6H_4]_2$, —$P[3,5$-bis(trifluoromethyl$)C_6H_3]_2$, —$P[3,5$-bis(methyl$)_2C_6H_3]_2$, —$P[3,5$-bis(methoxy$)_2C_6H_3]_2$ and —$P[3,5$-bis(methyl$)_{2\text{-}4}$-(methoxy$)C_6H_2]_2$ and groups of the formulae

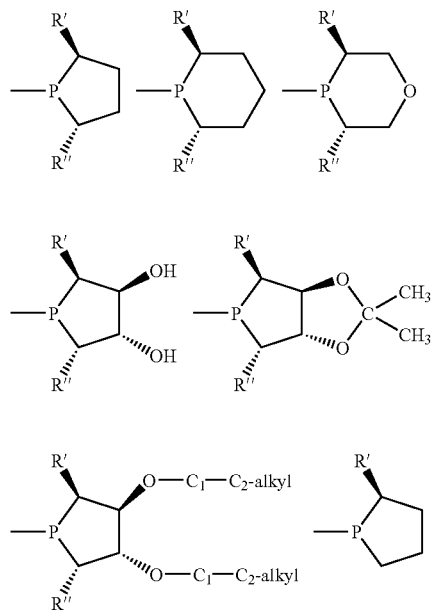
where
R' is methyl, ethyl, methoxy, ethoxy, phenoxy, benzyloxy, methoxymethyl, ethoxymethyl or benzyloxymethyl and R" has the same meanings as R'.
18. A compound of the formulae F, F', or F1 to F6,
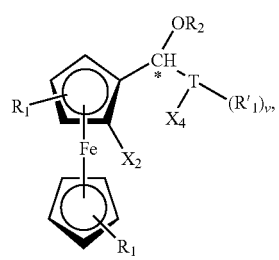
(F)
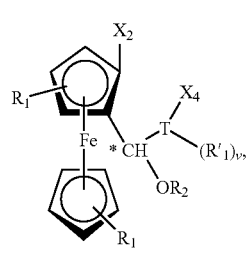
(F')
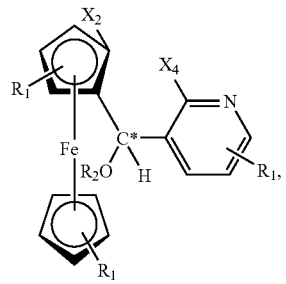
(F1)
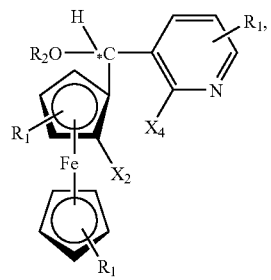
(F2)
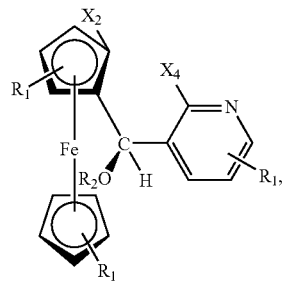
(F3)
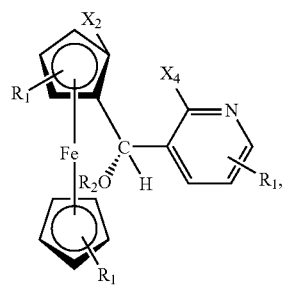
(F4)
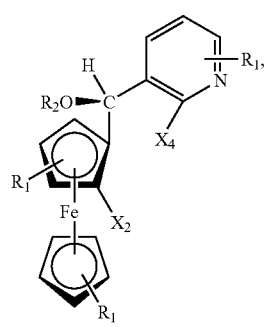
(F5)

-continued (F6)

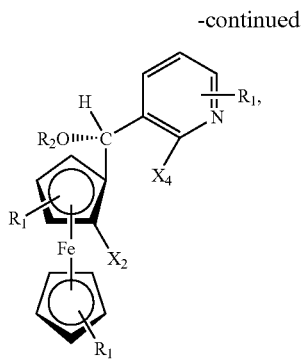

where
T is C-bonded $C_3$-$C_{20}$-heteroarylene,
$R_1$ are each, independently of one another, a hydrogen atom or $C_1$-$C_4$-alkyl,
$R'_1$ is $C_1$-$C_4$-alkyl,
$X_2$ is a sec-phosphino group,
v is 0 or an integer from 1 to 4,
$R_2$ is H and $X_4$ is Cl, Br or I.

19. A complex of a metal selected from among the group 8 transition metals with a compound of the formula I or I' according to claim 1 as a ligand.

20. A metal complex according to claim 19, wherein the group 8 transition metal is platinum, palladium, rhodium, iridium or ruthenium.

21. A metal complex according to claim 19, which corresponds to the formulae II or III, $$A_1 MeL_n \quad (II),$$

$$(A_1 MeL_n)^{(z+)(E-)}{}_z \quad (III),$$

where $A_1$ is one of the compounds of the formula I or I',
L represents identical or different monodentate, anionic or nonionic ligands, or L represents identical or different bidentate, anionic or nonionic ligands;
n is 2, 3 or 4 when L is a monodentate ligand or n is 1 or 2 when L is a bidentate ligand;
z is 1, 2 or 3;
Me is a metal selected from the group consisting of Rh, Ir and Ru; with the metal being in the oxidation state 0, 1, 2, 3 or 4;
$E^-$ is the anion of an oxo acid or complex acid; and
the anionic ligands balance the charge of the oxidation state 1, 2, 3 or 4 of the metals.

22. A metal complex according to claim 20, which corresponds to the formulae IV or V, $$[A_1 Me_2 YZ] \quad (IV),$$

$$[A_1 Me_2 Y]^+ E_1^- \quad (V),$$

where
$A_1$ is one of the compounds of the formula I or I';
$Me_2$ is rhodium or iridium;
Y represents two olefins or one diene;
Z is Cl, Br or I; and
$E_1^-$ is the anion of an oxo acid or complex acid.

23. A process for preparing a chiral organic compound by asymmetric addition of hydrogen onto a carbon-carbon or carbon-heteroatom double bond in a prochiral organic compound in the presence of a catalyst, wherein the addition reaction is carried out in the presence of a catalytic amount of at least one metal complex according to claim 19.

24. A complex of a metal selected from among the group 8 transition metals with a compound of the formula Ia to If as a ligand, (Ia)

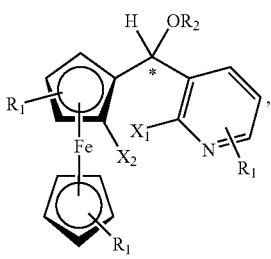

(Ib)

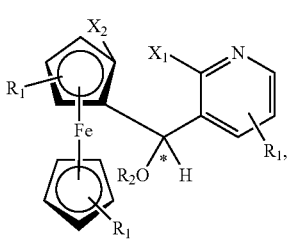

wherein $R_1$, $X_1$, $X_2$ and $R_2$ and * have the meanings given in claim 1, (Ic)

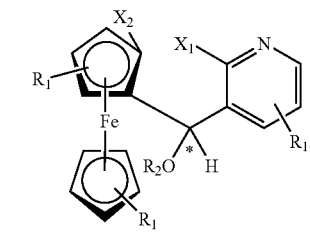

(Id)

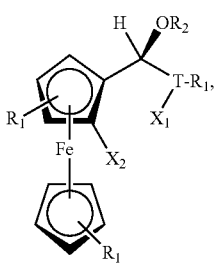

(Ie)

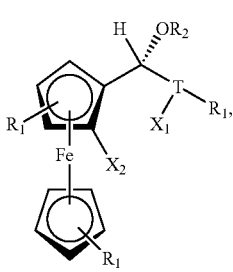

-continued
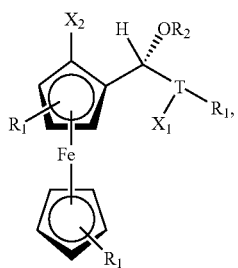
(If)
where
R₁ is hydrogen and T, R₂, X₁ and X₂ have the meanings given in claim 1.
25. A metal complex according to claim 24, wherein the group 8 transition metal is platinum, palladium, rhodium, iridium or ruthenium.
* * * * *